US009896728B2

(12) United States Patent
Zanke et al.

(10) Patent No.: US 9,896,728 B2
(45) Date of Patent: *Feb. 20, 2018

(54) METHOD FOR DETERMINING A THERAPEUTIC APPROACH FOR THE TREATMENT OF AGE-RELATED MACULAR DEGENERATION (AMD)

(71) Applicant: ArcticDx Ltd., Toronto (CA)

(72) Inventors: Brent Zanke, Toronto (CA); Carl Awh, Nashville, TN (US)

(73) Assignee: ArcticRx Ltd., Toronto, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/955,502

(22) Filed: Jul. 31, 2013

(65) Prior Publication Data

US 2014/0212507 A1 Jul. 31, 2014

Related U.S. Application Data

(60) Provisional application No. 61/757,981, filed on Jan. 29, 2013, provisional application No. 61/761,432, filed on Feb. 6, 2013, provisional application No. 61/777,681, filed on Mar. 12, 2013, provisional application No. 61/819,858, filed on May 6, 2013.

(51) Int. Cl.
*C12Q 1/68* (2006.01)

(52) U.S. Cl.
CPC ..... *C12Q 1/6883* (2013.01); *C12Q 2600/106* (2013.01); *C12Q 2600/156* (2013.01)

(58) Field of Classification Search
CPC ................ C12Q 1/68; C12Q 2600/106; C12Q 2600/156
See application file for complete search history.

(56) References Cited

FOREIGN PATENT DOCUMENTS

WO WO 2007/029008 A2 3/2007
WO WO 2010/085542 A2 7/2010

OTHER PUBLICATIONS

Li, M. et al. Nature Genetics 38(9):1049 (Sep. 2006; online Aug. 2006).*
Fritsche, L.G. et al. Nature Genetics 40(7):892 (Jul. 2008; online May 2008).*
Kovach, J.L. and Scott, I.U. "Update on clinical genetic testing for AMD", Article ID 106586, retinalphysician.com/printarticle (Jan. 1, 2012).*
European Search Report for Application No. EP13179087A1 dated Sep. 17, 2013.

(Continued)

*Primary Examiner* — Diana B Johannsen
(74) *Attorney, Agent, or Firm* — David Bradin; Andrews Kurth Kenyon LLP

(57) ABSTRACT

Disclosed is a method for determining a supplement regime for a subject diagnosed with age-related macular degeneration (AMD). The method involves determining the subject's risk of developing advanced AMD based on their genetic profile for the complement factor H gene and the ARMS2 gene and administering a supplement containing antioxidants and/or zinc based on their risk of developing advanced AMD.

6 Claims, 16 Drawing Sheets

| Genotype 9 | Time (years) | | | |
|---|---|---|---|---|
| AREDS Rx | 0 | 2 | 5 | 10 |
| Placebo | 0.0 | 34.6 | 73.1 | 89.8 |
| AO | 0.0 | 39.5 | 60.4 | 88.0 |
| Z/C | 0.0 | 20.5 | 36.4 | 73.5 |
| Z/C +AO | 0.0 | 17.7 | 41.1 | 66.1 |

(56) References Cited

OTHER PUBLICATIONS

Brantley, M. A., et al., "Association of Complement Factor H and LOC387715 Genotypes with Response of Exudative Age-Related Macular Degeneration to Intravitreal Bevacizumab," *Ophthalmology*, 2007, pp. 2168-2173, vol. 144(12), J.B. Lippincott Co.

Guan, H., et al., "Featured distribution of AMD-susceptibility SNPs between ethnicities and the modifying effect of SNPs on AMD therapy," *Expert Review of Ophthalmology*, 2009, pp. 377-386, vol. 4(4), Expert Reviews Ltd.

Klein, M. L., et al., "CFH and LOC387715/ARMS2 Genotypes and Treatment with Antioxidants and Zinc for Age-Related Macular Degeneration," *Ophthalmology*, 2008, pp. 1019-1025, vol. 115(6), J.B. Lippincott Co.

Lee, A. Y., et al., "Pharmacogenetics of complement factor H (Y402H) and treatment of exudative age-related macular degeneration with ranibizumab," *British Journal of Ophthalmology*, 2009, pp. 610-613, vol. 93(5).

Lotery, A. and D. Trump, "Progress in defining the molecular biology of age related macular degeneration." *Human Genetics*, pp. 219-236, vol. 122(3-4), Springer.

Schwartz, S. G. and M.A. Brantley, Jr., "Pharmacogenetics and Age-Related Macular Degeneration," *Journal of Ophthalmology*, 2011, pp. 4072-4078, vol. 52(7).

Seddon, J. M., et al., "Prediction Model for Prevalence and Incidence of Advanced Age-Related Macular Degeneration Based on Genetic, Demographic, and Environmental Variables," *Investigative Ophthalmology & Visual Science*, 2009, pp. 2044-2053, vol. 50(5).

* cited by examiner (A) rs3766405

CTGGACATTTTATATAGTGTGGGCTG[C/T]AACTTAAGTTTCACCGGGTGTGTCT
(SEQ ID NO.: 1)

(B) rs412852

AGAAACCAGTTCAAAGCCTCCTGCAA[C/T]CCCCTAAAGTAAACAGAGACCAATA
(SEQ ID NO.: 2)

(C) rs1061170

ATTTGGAAAATGGATATAATCAAAAT[C/T]ATGGAAGAAAGTTTGTACAGGGTAA
(SEQ ID NO.: 3)

(D) rs2274700

ACATATCCTAGTTTGCATTGATATTT[A/C/G/T]GCTTTTTCTTTTAAGGCATATGTAT
(SEQ ID NO.: 4)

(E) rs403846

CTTTGCTTCTCAGTGCCTAAAAAGGA[A/G]TACCATACAATAACAATAATATTTA
(SEQ ID NO.: 5)

(F) rs12144939 tttctatttcctctgaattaatcgtc[A/G/T]taggctgtgtgtctagaaatttatc
(SEQ ID NO.: 6)

(G) rs1409153

CATAAAATGATTAAAAGGTAGATTAG[A/G]AACATGAATTTGATCAAAATAGTAT
(SEQ ID NO.: 7)

(H) rs1750311

TTTCTAAATTTTTTTTCAGTGGGATG[A/C]TATGTTGATAGCAGCTACTCCATCC
(SEQ ID NO.: 8)

(I) rs10922153

TTTGAAACTTTCTGAATTAACGTTAT[G/T]TAAAAGGAAATGTAGATGTTATTTT
(SEQ ID NO.: 9)

TCTAAATTATTTGTGCTGAACATTTC[A/G]TTATTTATAAATGAAAACCAATAAA
(SEQ ID NO.: 10)

(K) rs2990510

TAAGTAGAGCAATGCTTTACAGTGTT[G/T]GTTGTTGAGTGCTCACAAGAAGGTG
(SEQ ID NO.: 11)

(L) rs3753394

AAGGGTTTATGAAATCCAGAGGATAT[C/T]ACCAGCTGCTGATTTGCACATACCA
(SEQ ID NO.: 12)

(M) rs529825

GTAACCTTGGCAATGGGTAAGTCTAT[C/T]GTACTGTGTAAACTTGGACTACCTC
(SEQ ID NO.: 13)

(N) rs800292

TTCTCCCTTCCTGCATACCATTATTA[C/T]ATTTCCAAGAGATCTATATCCAGGG
(SEQ ID NO.: 14)

(O) rs3766404

AAGAAAAAAGGAATACATTTAGGACT[C/T]ATTTGAAGTTAGTGTCAACATCAAA
(SEQ ID NO.: 15)

(P) rs1061147

TATCCTGCAACCCGGGGAAATACAGC[A/C]AAATGCACAAGTACTGGCTGGATAC
(SEQ ID NO.: 16)

(Q) rs2033674

ACACACCATACCTTGGTTACATACAA[G/T]TCATATTTTATCATATTTTTAGTAA
(SEQ ID NO.: 17)

(R) rs3753396

CTAATGAAGGGACCTAATAAAATTCA[A/G]TGTGTTGATGGAGAGTGGACAACTT
(SEQ ID NO.: 18)

FIG. 1A (S) rs1065489

GGCCTTCCTTGTAAATCTCCACCTGA[G/T]ATTTCTCATGGTGTTGTAGCTCACA (SEQ ID NO.: 19)

(T) ARMS2

ACAAAAAAAC AACAAAAAAT CCCAAAACCC CCAAAACTCT CATTGACCCT TATCTCAGAT 60
TTCCCGAATG CTTACCACCC TCGCTACATC ATTCAAGTTC TTGGAAACAT TTAAAGCATG 120
TGAAACATTT AAAACATTTA AGTTGGAGGC TTTAAGTTGC ACGTCCTTTA TTTCTAAATA 180
TTTCAGTGTG TTTTTCTTAA AAAAAATTTT CTCATACCAC AGTAACATGA TCAAAATTGG 240
AAAATCAACA TTGATTCAAT ACTATGATCT ACAATCAAGG TTTTTTTTTT TTTTCAAATC 300
CCTGGGTCTC TGCATTTTTT AAAAGCTTCA CAGATGATTT CAATGGATAC TAGGGACCTC 360
TGTTGCCTCC TCTGGCAGAG CAGGACTGAG GGGTGGACCC TCCCTGAGAC CACCCAACAA 420
TTCAGGGTGG AGTTATCAGG GCGCCCTGAC TCCTGGGGGC ATTTTTGTGT GACGGGAAAA 480
GACAATGCTC CTGGCTGAGT GAGATGGCAG CTGGCTTGGC AAGGGGACAG CACCTTTGTC 540
ACCACATTAT GTCCCTGTAC CCTACATGCT GCGCCTATAC CCAGGACCGA TGGTAACTGA 600
GGCGGAGGGG AAAGGAGGGC CTGAGATGGC AAGTCTGTCC TCCTCGGTGG TTCCTGTGTC 660
CTTCATTTCC ACTCTGCGAG AGTCTGTGCT GGACCCTGGA GTTGGTGGAG AAGGAGCCAG 720
TGACAAGCAG AGGAGCAAAC TGTCTTTATC ACACTCCATG ATCCCAGCTG CTAAAATCCA 780
CACTGAGCTC TGCTTACCAG CCTTCTTCTC TCCTGCTGGA ACCCAGAGGA GGTTCCAGCA 840
GCCTCAGCAC CACCTGACAC TGGTAAGAAA TGCAGATGAT CAGGCCTTAC CCCAGACCTA 900
TTGAATCAGA AATTCTGGAG TGGTGCCCTG CAGCTTGCAT TTTAACCAGC CTTCAGGTGC 960
TTCTGATGCA TGCTCAGGTT TGAGCACCAC TGGCCACAGG GAGGCCTAGG CAATTCAGCC 1020
TTCCTCTGGT TGAATAGCTG GAGAATTGGG AATATCAGTA AATACTTCCA ATGCACCTGC 1080
TACATGCCAG AAAAAGGAAA CAAGAAGACG CAGTAGGTCT GAGAAAGTGA TGGGGTGAGC 1140
AGAAACCCAA AGCTTATAGA AGGCCATCTG AGTGGCCCCT CAAGCCGGTG AATTGGCTTT 1200
AGGGTTTACT GAAGGAGGTG GAAACCTCAG CCTGCTTCTC GTCCGGGTTG TTAGAGGAGT 1260

FIG. 1B

```
CATTTAGAAA GCTGTACCAT TCTTTCAATA TTCTCACGGC TTTCCAGTGC TCATTTTTCC     1320
TGCTCATTTA TGGATTAAAA AAAATGCCTT GGCTGTATGT GTAAGAAAAC AACAATGCAA     1380
GTTTGTAGAG AAAGAATCTG GGCCTTACAG GTCACGTTGG TTTAAAATTT AGACATCAAG     1440
CAGCTTAGAG ACCATGTTGC CAAATAAGCT TAGTAAATGC TTTCTAATGC TTACGGAACT     1500
GTGGCGCTTT GTGCTTGCCA TAGTATATAT AATTAGACAA ATGAGAGAAC ACAAAGGTTG     1560
AACCCCTTCC CTCTCTTAAT TTTTGTTTTT TACAAGCAGA TTTAAAATTC TGGCTCATAA     1620
TGTCCTTGAT TCAATGTTAA ACCATTTTGC CTAAATGGCA GCATGTTCTA AATGTGAGCG     1680
CGCTCAGCTT TTCAAGCTGC TCCCGAGTGA CAGAAATTGA CAAGCTGTCA TTCAAGACCT     1740
TTCGGTGGCT GCCTGGGGCT CTGTTTGAAT TGTATCTGTC TGATACTTTA CCATGGAGAG     1800
TGAAAAATTT GATCACATGC CATGCTTTTA ATTTTCTAAA GCAAATATGT TGGAAGGAGC     1860
CAATTAATGC AAAGATGGAC TGCTGGTCTC ATGCAACTGA TTTAGGGGAA GGGTTCGCCT     1920
AAATTAATAA AAGATCTGAA TTATAGATCT TAACAAATAC ATAGAATGTA AAGGCTTAAA     1980
AGGAAACTGA GCAGCAGCAG GCCTGGGGTT GGCTTTTAAG TATCTATATT TAACTAATAG     2040
ACATGAATGT TTTGATTTGA TATTAGAAAT GCTAGTGCTG GAGTCTCTGA GCCTACTCTG     2100
GCTCGAGAGG ATGCCCTATC TAAAAAACAA AAAACAAAAA AAAAAAAGAA AAAAGAAAAA     2160
AAGAAATGCT GGTATTGTAA TTCTAAAGTG CTTCAGAAAT TCTCAAAAAT AGGCCAGGCA     2220
TGGTGGCTCA TGGCTGTATA CCAGCACTTT GGGAGGCCAA GGTGGGCAAA TCACTTGCAG     2280
TCAGGAGTTT GAGACCAGCC TGGTCAACAT GGTGAAACCC CATCTCTACT AAAAATACAG     2340
AAATTAGCCA GGCATGGTGG CAGCACCTGT AATCCCAGCT ACTTGGGAGG CTGAGGCAGG     2400
AGAATCGCTA GAACCTGGGA GGTGGAGGTT GCAGTGAGCC AAGACCGCAC CACTGCACTC     2460
CAGCCTGGGC AACAGAGTGA GACTCTATCT CAAAAAAAAA AAAAAAAAGT TCTCAAAAGT     2520
ATTTTGAACT TCCTCACCTT TGTCCTATTT TGGAAGGAGG GGGTCTACAT TGAAGAGATC     2580
ATACAGAAAT AAATTAATTG TTACAAAAGG AATGGAATGT CTATACTTCT TACCCTATTG     2640
AGTTACATTA ACTGCATCTT CAACTTAATT TAAAGTGCTC CTCAACCTAA AATATCGTCA     2700
TGTGTCTTTA AAAATGCATA TTACTAAATC TATTTTTTTT TCAGTCTATC ATCCACACTG     2760
```

FIG. 1C

CAGCAAGGTG ATTCTGCCAA AACATATCTC CTTAAAAGCC AACTGGAGCT TCTCATCAGC 2820

ATCAATGTGA AGCCAAAAAT CCTTAGGAGG ACAGAGGGAG TCCCTCACAA CCTAGACTGG 2880

TCCCCTTCCC TCCAGCTGCC TCAACTGTCC ACAGGACTCT CTTCCCACCT GCGGCCACAC 2940

TGTGCAACCT GGAATTTCCC CACCTGGGCG GACTCATCAC GTCATCACCA ATTGGATGCA 3000

TCTTCTGCTC TGTGCAGCTG GTGAAATCTT TCTCAACCCT TGAGATGCAG CCCAATCTTC 3060

TCCTAACATC TGGATTCCTC TCTGTCACTG CATTCCCTCC TGTCATCCTG CCTTTGTTTT 3120

CTTGCCCTCC TTTCTCTCCC GGGTGATAGG CATTAACTAA AATTAAATAA AAATTCAGAT 3180

CATCCTTGCA CTTGCTGCAT TTCAAATGCT TGGCAGTCAC ATGTAGTTAG TGGCTACCCT 3240

CTTGGACAGC ACAGATAGAG ATTATTTCCA TCACTGCAGA AAATTCTAGA CTTTGAGCTT 3300

CTTGAGGACA GGGGCTTGAT CATTCGACAC TGCTTTACAG TGTCTAGCAG TGTCTACCCT 3360

GTGGCAGGGG CTCAGGAAAT TTTTCCTGAA CCGAACCTAA CTGAACTGAT GTGGGTTTGT 3420

CATCAGGGTG TACCTGCTGT TAAAGGAGGT TACGACCTCT GATGCTGGGG TGGCCAGAGG 3480

GGATGGGAGT GGGTCTGGCA CTCTGAGGAA AGGGGGTGAA ACCAGCTGAG AAGTCATCTT 3540

TTACCTGCTG GCATGGCCCC AGCCAGGGTT CTGTTGCTAT GGGAGAATGG GTGAGTAGGG 3600

ATGGATTACA CCACCCTGGA TCTAGAGGAC AACCTGGCTT GAGGGGCATG GGGGACGCTG 3660

GAAGTCAGGG TAAGAAGCTT GGACTTCATT 3690

(SEQ ID NO.:20)

(U) ARMS2 insertion

TTGAGATGCA GCCCAATCTT CTCCTAACAT CTGGATTCCT CTCTGTCACT GCATTCCCTC 60

CTGTCATCCT GCCTTTGTTT TCTTGCCCTC CTTTCTCTCC CGGTTATTAA TTAATTAACT 120

AAAATTAAAT TATTTAGTTA ATTTAATTAA CTAAACTAAT GGGTGAGTAG GGATGGATTA 180

CACCACCCTG GATCTAGAGG ACAACCTGGC TTGAGGGGCA TGGGGGACGC TGGAAGTCAG 240

GGTAAGAAGC TTGGACTTCA TTCTACTGGC ATGGAGAGCC CCTGGAAACT ACTGAGCAGT 300

AGAGGGATAG GCTAAGCTTA TAGGAGGAGC CAAAATTATT ACTGTAGCTC CTTAGATCTT 360

AGATCCTGTG ACTTAGGAAA GGCAATAGGA GCCCCTGAGC ATTCTGGGTC CTTTG 415

FIG. 1D (SEQ ID NO.:21)

(V) rs10490924

CTTTATCACACTCCATGATCCCAGCT[G/T]CTAAAATCCACACTGAGCTCTGCTT (SEQ ID NO.:22)

(W) rs1048663

TGACTTACCTCTAGAAGACTGAATAG[A/G]TATCAGGTCATCCTCCTGGATAATC (SEQ ID NO:23)

(X) rs11582939

TTTAAGCATCCTCTGATGTATATTCT[C/T]AGACTTCTCATCTCTGTTCTTAGGG (SEQ ID NO: 24)

(Y) rs1280514

CTCCTGCTCATTCCTCTCAACAGACA[A/G]AAACAATTTTGTGAGAATTTTTATG (SEQ ID NO: 25)

FIG. 1E

| Genotype 1 | Time (years) | | | |
|---|---|---|---|---|
| AREDS Rx | 0 | 2 | 5 | 10 |
| Placebo | 0.0 | 9.6 | 26.8 | 41.9 |
| AO | 0.0 | 12.7 | 22.1 | 43.6 |
| Z/C | 0.0 | 10.6 | 19.8 | 47.7 |
| Z/C +AO | 0.0 | 17.7 | 41.1 | 66.1 |

| Genotype 2 | Time (years) | | | |
|---|---|---|---|---|
| AREDS Rx | 0 | 2 | 5 | 10 |
| Placebo | 0.0 | 23.7 | 56.8 | 76.7 |
| AO | 0.0 | 33.5 | 52.8 | 82.2 |
| Z/C | 0.0 | 10.6 | 19.8 | 47.7 |
| Z/C +AO | 0.0 | 17.7 | 41.1 | 66.1 |

| Genotype 4 | Time (years) | | | |
|---|---|---|---|---|
| AREDS Rx | 0 | 2 | 5 | 10 |
| Placebo | 0.0 | 34.6 | 73.1 | 89.8 |
| AO | 0.0 | 39.5 | 60.4 | 88.0 |
| Z/C | 0.0 | 10.6 | 19.8 | 47.7 |
| Z/C +AO | 0.0 | 17.7 | 41.1 | 66.1 |

| Genotype 3 | Time (years) | | | |
|---|---|---|---|---|
| AREDS Rx | 0 | 2 | 5 | 10 |
| Placebo | 0.0 | 9.6 | 26.8 | 41.9 |
| AO | 0.0 | 12.7 | 22.1 | 43.6 |
| Z/C | 0.0 | 11.8 | 22.0 | 51.7 |
| Z/C +AO | 0.0 | 17.7 | 41.1 | 66.1 |

| Genotype 5 | Time (years) | | | |
|---|---|---|---|---|
| AREDS Rx | 0 | 2 | 5 | 10 |
| Placebo | 0.0 | 23.7 | 56.8 | 76.7 |
| AO | 0.0 | 33.5 | 52.8 | 82.2 |
| Z/C | 0.0 | 11.8 | 22.0 | 51.7 |
| Z/C +AO | 0.0 | 17.7 | 41.1 | 66.1 |

| Genotype 7 | Time (years) | | | |
|---|---|---|---|---|
| AREDS Rx | 0 | 2 | 5 | 10 |
| Placebo | 0.0 | 34.6 | 73.1 | 89.8 |
| AO | 0.0 | 39.5 | 60.4 | 88.0 |
| Z/C | 0.0 | 11.8 | 22.0 | 51.7 |
| Z/C +AO | 0.0 | 17.7 | 41.1 | 66.1 |

| Genotype 6 | Time (years) | | | |
|---|---|---|---|---|
| AREDS Rx | 0 | 2 | 5 | 10 |
| Placebo | 0.0 | 9.6 | 26.8 | 41.9 |
| AO | 0.0 | 12.7 | 22.1 | 43.6 |
| Z/C | 0.0 | 20.5 | 36.4 | 73.5 |
| Z/C +AO | 0.0 | 17.7 | 41.1 | 66.1 |

| Genotype 8 | Time (years) | | | |
|---|---|---|---|---|
| AREDS Rx | 0 | 2 | 5 | 10 |
| Placebo | 0.0 | 23.7 | 56.8 | 76.7 |
| AO | 0.0 | 33.5 | 52.8 | 82.2 |
| Z/C | 0.0 | 20.5 | 36.4 | 73.5 |
| Z/C +AO | 0.0 | 17.7 | 41.1 | 66.1 |

| Genotype 9 | Time (years) | | | |
|---|---|---|---|---|
| AREDS Rx | 0 | 2 | 5 | 10 |
| Placebo | 0.0 | 34.6 | 73.1 | 89.8 |
| AO | 0.0 | 39.5 | 60.4 | 88.0 |
| Z/C | 0.0 | 20.5 | 36.4 | 73.5 |
| Z/C +AO | 0.0 | 17.7 | 41.1 | 66.1 |

METHOD FOR DETERMINING A THERAPEUTIC APPROACH FOR THE TREATMENT OF AGE-RELATED MACULAR DEGENERATION (AMD)

FIELD OF THE INVENTION

The present invention relates to the fields of age-related macular degeneration (AMD) predictive testing and therapeutics. In particular, the invention relates to a method for determining a supplement regime in a subject with AMD.

BACKGROUND OF THE INVENTION

Age-related macular degeneration (AMD) causes progressive impairment of central vision and is the leading cause of irreversible vision loss in older Americans (Swaroop A et al., 2007, Hum Mol Genet 16 Spec 2:R174-82). Some subjects with dry AMD will have the disease progress into neovascular or exudative AMD, which usually results in blindness. The neovascular or exudative form of AMD is also referred to as wet AMD. Other patients with dry AMD may progress to central geographic atrophy of the retina. Wet AMD and central geographic atrophy are both classified as “advanced AMD”.

Although the etiology of AMD remains largely unknown, implicated risk factors include: age, ethnicity, smoking, hypertension, obesity and diet (Ambati J et al., 2003, Surv Ophthalmol 48(3):257-93). Familial aggregation (Klayer C C et al., 1998, Arch Ophthalmol 116(5):653-8), twin studies (Hammond C J et al., 2002, Ophthalmology 109(4):730-6), and segregation analysis (Heiba I M et al., 1994, 11(1):51-67) suggest that there is also a significant genetic contribution to the disease. The candidate gene approach and genome-wide association studies have consistently implicated the complement factor H (CFH), third component of complement (C3) and second component of complement/factor B (C2/BF) genes, all members of the complement-mediated inflammatory cascade, as well as Age-Related Maculopathy Susceptibility 2 (ARMS2), a gene likely involved in mitochondria-associated pathways.

Much progress has been made in identifying and characterizing the genetic basis of AMD. In a remarkable example of the convergence of methods for disease gene discovery, multiple independent research efforts identified the Y402H variant in the complement factor H (CFH [(MIM 134370]) gene on chromosome 1q32 as the first major AMD susceptibility allele (Haines J L et al., 2005, Science 308(5720):419-21; Hageman G S et al., 2005, Proc Natl Acad Sci USA 102(20):7227-32; Klein R J et al., 2005, Science 308(5720):385-9; Edwards A O et al., 2005, Science 308(5720):421-4; Zareparsi S et al., 2005, Am J Hum Genet 77(1):149-53; Jakobsdottir J et al., 2005, Am J Hum Genet 77(3):389-407). While one of the studies was able to pinpoint CFH on the basis of a whole-genome association study (Klein R J et al., supra), most studies focused on the 1q32 region because it had consistently been implicated by several whole-genome linkage scans. More recently, disease associated haplotypes within the CFH gene have also been shown to be associated with AMD (Li M et al., 2006, Nat Genet 38(9):1049-54). A second genomic region with similarly consistent linkage evidence is chromosome 10q26, which was identified as the single most promising region by a recent meta-analysis of published linkage screens (Fisher S A et al., 2005, Hum Mol Genet 14(15):2257-64).

The Age-Related Eye Disease Study (AREDS), sponsored and conducted by the National Eye Institute in the United States, provided descriptive data on the clinical course of AMD and attempted to identify factors that influence the development of early disease and progression and evaluated the potential efficacy of high-dose vitamins and minerals to arrest or retard disease progression. AREDS was a long-term multicenter, prospective study of 4757 persons age 55 to 80 years that assessed the clinical course, prognosis, and risk factors of AMD.

The study was designed to document the clinical course of AMD and determine progression risk determinants through the collection of data on possible risk factors, Changes in visual acuity, photographically documenting changes in the macula and self-reported visual function were recorded at regular intervals. A grading system was developed for each of the lesions of AMD. The major AMD outcomes in this study were the development of neovascular disease or the development of geographic atrophy that involves the center of the macula. Eyes developing either of these conditions were considered to have progressed to advanced AMD. Early lesions of AMD, particularly drusen (size, type, and extent) and RPE abnormalities (detachment, atrophy, and pigment disturbances) were graded individually for each study eye.

At the time of the AREDS study design there was evidence for the beneficial effect of elemental zinc for AMD. The study was designed to determine if zinc, alone or in combination with a vitamin/antioxidant formulation could slow the progression of AMD. Formulations that included zinc included copper to prevent zinc-induced copper-deficiency anemia. Study participants at risk of vision loss with early AMD received combinations of the zinc formulation and the vitamin/antioxidant formulation. Participants without drusen or RPE changes were never assigned to the zinc formulation. Remaining participants (3640) were enrolled in a 2×2 factorial design of antioxidants and zinc.

The results of the AREDS Study were reported in 2001 (see AREDS report no. 8, Arch Ophthalmol 119:1417-36, 2001, which is incorporated herein in its entirety). The average follow-up of the 3640 enrolled study participants, aged 55-80 years, was 6.3 years, with 2.4% lost to follow-up. Compared with placebo, treatment with antioxidants plus zinc demonstrated a statistically significant odds reduction for the development of advanced AMD (odds ratio [OR], 0.72; 99% confidence interval [CI], 0.52-0.98). The ORs for zinc alone and antioxidants alone are 0.75 (99% CI, 0.55-1.03) and 0.80 (99% CI, 0.59-1.09), respectively. Participants with extensive small drusen, nonextensive intermediate size drusen, or pigment abnormalities had only a 1.3% 5-year probability of progression to advanced AMD. Odds reduction estimates increased when these 1063 participants were excluded (antioxidants plus zinc: OR, 0.66; 99% CI, 0.47-0.91; zinc: OR, 0.71; 99% CI, 0.52-0.99; antioxidants: OR, 0.76; 99% CI, 0.55-1.05). Both zinc and antioxidants plus zinc significantly reduced the odds of developing advanced AMD in this higher-risk group. The only statistically significant reduction in rates of at least moderate visual acuity loss occurred in persons assigned to receive antioxidants plus zinc (OR, 0.73; 99% CI, 0.54-0.99). No statistically significant serious adverse effect was associated with any of the formulations.

As a result of the findings of AREDS study, subjects or patients that present with the symptoms of dry AMD are routinely prescribed zinc and antioxidant containing vitamins to slow or prevent the onset of wet AMD. The genetic profile of the subject has not been a consideration when prescribing such course of treatment.

SUMMARY OF THE INVENTION

According to an aspect of the present invention there is provided a method for determining a supplement regime for a subject diagnosed with age-related macular degeneration (AMD). The method involves determining the subject's risk of advanced AMD in a sample from the subject based on their genetic profile for the complement factor H gene; and administering a supplement based on their genetic profile for the complement factor H gene. When the subject is at high risk of developing advanced AMD based on their genetic profile for the complement factor H gene (2 risk alleles) the supplement is free from zinc and/or copper. When the subject is at low risk of developing advanced AMD based on their genetic profile for the complement factor H (CFH) gene (no risk alleles) the supplement comprises zinc and/or copper.

In one embodiment, the subject diagnosed with age-related macular degeneration has one or more retinal drusen.

In another embodiment, the subject's risk of developing advanced AMD is determined by analysing the single nucleotide polymorphisms: rs3766405 and rs412852 in the CFH gene.

In a further embodiment, the subject's risk of developing advanced AMD is determined by analysing the single nucleotide polymorphisms: rs1048663, rs3766405, rs412852, rs11582939 and/or rs1280514 in the CFH gene.

In a still further embodiment, the subject's risk of developing advanced AMD is determined by analysing the single nucleotide polymorphism rs1061170, where an individual is at high risk of developing advanced AMD when they are homozygous for the C allele, at medium risk when they are heterozygous for the C allele and at low risk when they are homozygous for the T allele.

In yet another embodiment, the subject's risk of developing advanced AMD may be determined by analysing the single nucleotide polymorphisms: rs1061170, rs2274700, rs403846, rs12144939, rs1409153, rs1750311, rs10922153, rs698859, rs2990510, rs3753394, rs529825, rs800292, rs3766404, rs1061147, rs2033674, rs3753396, and/or rs1065489 in the CFH gene. These single nucleotide polymorphisms may be used alone, in combination with each other, and/or with one or more additional single nucleotide polymorphisms in the CFH gene.

In yet a further embodiment, the supplement is a multivitamin and mineral supplement.

In another embodiment, when the subject is at high risk of advanced AMD based on their genetic profile for the complement factor H gene the supplement is also free from zinc and/or copper. In addition, when the subject is at low risk of developing advanced AMD based on their genetic profile for the complement factor H (CFH) gene the supplement also contains zinc.

In an embodiment, the subject is considered at high risk of developing advanced AMD when the subject is homozygous for the C allele at rs3766405 and is homozygous for the C allele at rs412852. The subject is considered at medium risk of developing advanced AMD when the subject is heterozygous for the C allele at rs3766405 and is heterozygous for the C allele at rs412852; or homozygous for the C allele at rs3766405 and heterozygous for the T allele at rs412852. The subject is considered at low risk of developing advanced AMD when the subject is homozygous for the C allele at rs3766405 and is homozygous for the T allele at rs412852, heterozygous for the C allele at rs3766405 and is homozygous for the C allele at rs412852, heterozygous for the C allele at rs3766405 and is homozygous for the T allele at rs412852, homozygous for the T allele at rs3766405 and is homozygous for the C allele at rs412852, homozygous for the T allele at rs3766405 and is heterozygous for the C allele at rs412852 or homozygous for the T allele at rs3766405 and is homozygous for the T allele at rs412852.

In further embodiments, the subject is considered at risk of developing advanced AMD when: the subject has the C allele at rs1061170; the subject has the G allele at rs2274700; the subject has the A allele at rs403846; the subject has the G allele at rs12144939; the subject has the G allele at rs1409153; the subject has the C allele at rs1750311; the subject has the G allele at rs10922153; the subject has the A allele at rs698859; the subject has the T allele at rs2990510; the subject has the C allele at rs3753394; the subject has the C allele at rs529825; the subject has the T allele at rs800292; the subject has the C allele at rs3766404; the subject has the A allele at rs1061147; the subject has the T allele at rs2033674; the subject has the G allele at rs3753396; and/or the subject has the T allele at rs1065489 in the CFH gene. Risk is considered high if the subject is homozygous for the allele, and medium if the subject is heterozygous for the allele.

In another embodiment, the method includes determining the subject's risk of developing advanced AMD based on their genetic profile for the Age-Related Maculopathy Susceptibility 2 (ARMS2) gene. The genetic profile of the subject at the ARMS2 gene can be used to further delineate the optimal supplement composition for the subject to reduce the chances of their condition developing into advanced AMD.

The subject is considered at high risk of developing advanced AMD when the subject is homozygous for the insertion/deletion polymorphism, considered at medium risk when the subject is heterozygous for the insertion/deletion polymorphism and is considered at low risk when the subject does not have the insertion/deletion polymorphism. The insertion/deletion polymorphism being defined as a deletion of a nucleic acid sequence from position 3143 of SEQ ID NO: 20 to position 3585 of SEQ ID NO: 20 and insertion of a sequence from position 104 of SEQ ID NO: 21 to position 157 of SEQ ID NO: 21 in place of the deleted sequence. Alternatively, the genetic profile of the subject at rs104890924 in the ARMS2 gene can be used to determine the subject's risk of developing advanced AMD.

When the subject has 2 high risk alleles at the complement factor H gene and has no high risk ARMS2 risk alleles, then the subject is administered a supplement that comprises antioxidants and is free from zinc and/or copper.

When the subject has 2 high risk alleles at the complement factor H gene and has one high risk ARMS2 risk allele, then the subject is administered a supplement that comprises at least antioxidants. However, the supplement can also contain zinc and/or copper.

When the subject has 1 high risk allele at the complement factor H gene and has no high risk ARMS2 risk alleles, then the subject is administered a supplement that comprises antioxidants and is free from zinc and/or copper.

When the subject has 1 high risk alleles at the complement factor H gene and has one high risk ARMS2 risk allele, then the subject is administered a supplement that comprises zinc and/or copper and antioxidants.

When the subject has no risk complement factor H alleles and has 0 risk alleles for the ARMS2 gene, then the subject is administered a supplement that contains zinc and/or copper.

When the subject has no risk complement factor H alleles and has 1 risk alleles for the ARMS2 gene, then the subject is administered a supplement that contains zinc and/or copper and is free of antioxidants.

When the subject has no risk complement factor H alleles and has 2 risk alleles for the ARMS2 gene, then the subject is administered a supplement that contains zinc and/or copper and is free of antioxidants.

When the subject has 1 complement factor H risk alleles and 2 risk alleles for the ARMS2 gene, then the subject is administered a supplement that contains zinc and/or copper and is free of antioxidants.

When the subject has 2 complement factor H risk alleles and 2 risk alleles for the ARMS2 gene, then the subject is administered a supplement that contains antioxidants. However, the supplement could also contain zinc and/or copper.

According to the method described above, the subject's genetic profile can be detected by hybridization, chemical cleavage, direct DNA sequencing, use of restriction enzymes or Southern blotting.

BRIEF DESCRIPTION OF THE DRAWINGS

These and other features, aspects and advantages of the present invention will become better understood with regard to the following description and accompanying drawings wherein:

FIGS. 1-1E represent the nucleotide sequences containing (A) rs3766405, (B) rs412852, (C) rs1061170, (D) rs2274700, (E) rs403846, (F) rs12144939, (G) rs1409153, (H) rs1750311, (I) rs10922153, (J) rs698859, (K) rs2990510, (L) rs3753394, (M) rs529825, (N) rs800292, (0) rs3766404, (P) rs1061147, (Q) rs2033674, (R) rs3753396, (S) rs1065489, (T) ARMS2, (U) ARMS2 insertion, (V) rs10490924, (W) rs1048663, (X) rs11582939, and (Y) rs1280514;

DESCRIPTION OF THE INVENTION

Figure 2:
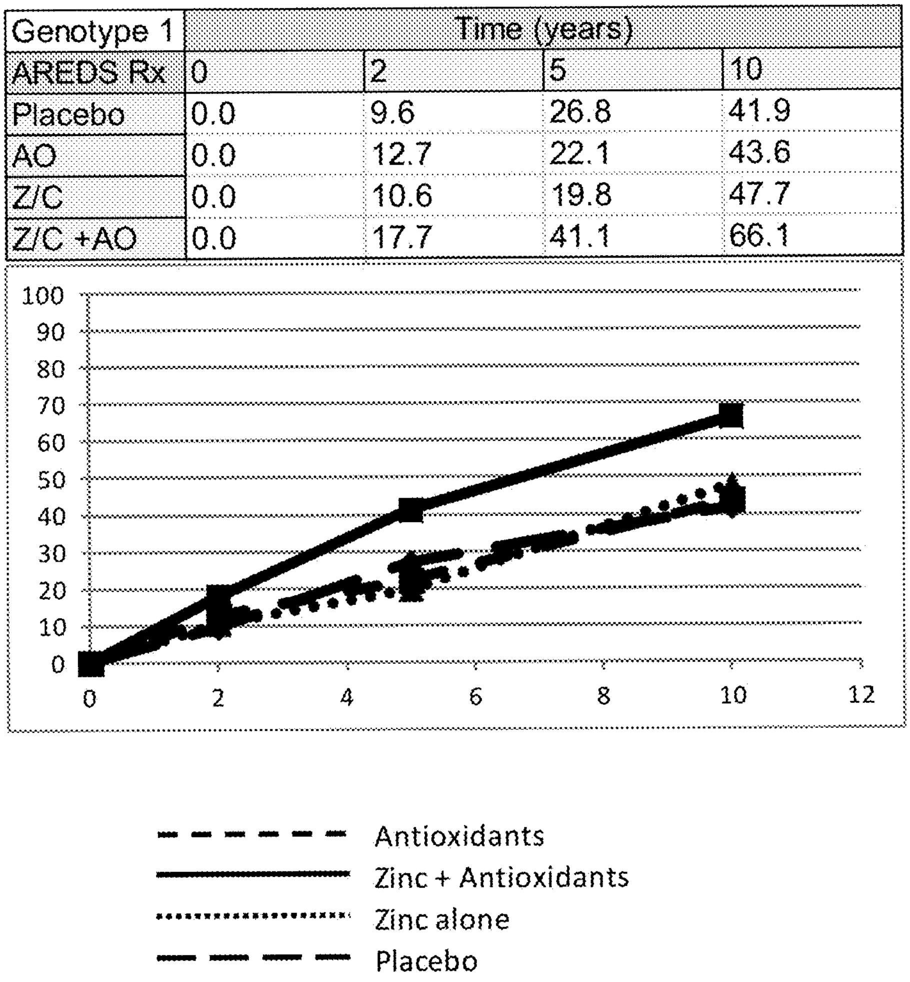
FIG. 2 is a graphical representation of the percentage of subjects having no CFH and no ARMS2 risk alleles estimated to progress from AREDS category 3 disease in at least one eye to AREDS category 4 disease in the eye that initially had category 3 disease. The graph shows the variable "Time" on the X axis and "Percent Progressing" on the Y axis.

The following description is of an illustrative embodiment by way of example only and without limitation to the combination of features necessary for carrying the invention into effect.

The method described herein is purposed to determine a supplement regime for a subject that has been diagnosed previously with age-related macular degeneration characterized by one or more drusen in one or both eyes, or is concurrently (i.e. for the first time) being diagnosed with this form of the disease. For the purposes of this disclosure, the term "dry AMD" will be used hereinafter to describe the condition characterized by retinal drusen. For the purposes of this disclosure, the term "wet AMD" will be used hereinafter to describe the neovascular or exudative form of AMD. Central Geographic Atrophy and wet AMD are conditions classified as "advanced AMD".

The method described herein analyses the genetic profile of the subject to determine whether a supplement regime containing zinc and/or antioxidants should be administered to the subject, or whether the supplement regime should be free from zinc or antioxidants. For example, a subject having AMD with one or more drusen in one or both eyes, and a genetic profile of two complement factor H AMD risk alleles should avoid being administered a supplement containing zinc. A subject having AMD with one or more drusen in one or both eyes and a genetic profile having 1 complement factor H risk allele and 1 or 2 ARMS2 risk alleles should be prescribed a supplement regime without antioxidants in order to prolong the potential onset of advanced AMD. Similarly, those individuals having AMD with one or more drusen in one or both eyes and no high risk AMD CFH risk alleles should be prescribed a supplement regime that includes zinc. For the purposes of this discussion, the supplement can include also copper. Since copper is usually included with any vitamin formulation that includes zinc, it is possible that copper may be responsible for the therapeutic benefit normally achieved with zinc.

The supplement regime described herein can be in the form of a single multiple vitamin formulation, or can be a series of individual vitamin formulations, or combinations thereof. In either case, the formulation should be controllable so that zinc and/or antioxidants can be provided or removed depending on the specific needs of the patient.

Antioxidants and the dosages thereof that provide health benefits are known to those skilled in the art, and often include, but are not limited to, vitamins C and E, selenium, and carotenoids, such as beta-carotene, lycopene, lutein, and zeaxanthin. For the purposes of the present discussion antioxidants can be synthetic or be derived from natural sources. Zinc supplements can include zinc oxide or any other zinc-containing salt or compound with or without copper.

In a subject already having AMD characterized by one or more drusen in one or both eyes, the risk of developing advanced AMD is determined by the genetic profile of the subject. In particular, single nucleotide polymorphisms (SNPs) in the complement factor H (CFH) gene located on chromosome 1 of the human genome are used to determine the risk of the subject developing advanced AMD. Several SNPs in the CFH gene are predictors of AMD development and/or predictors of disease progression from early forms of the disease to advanced AMD (Li M et al., Nature Genetics 38(9):1049-1054, 2006, the contents of which are incorporated herein). These SNPs include: rs1048663 (SEQ ID NO: 23), rs3766405 (SEQ ID NO: 1), rs412852 (SEQ ID NO: 2), rs11582939 (SEQ ID NO: 24) and rs1280514 (SEQ ID NO: 25). In the method described herein, at least rs3766405 (SEQ ID NO: 1) and rs412852 (SEQ ID NO: 2) are used to determine the risk of a subject with AMD characterized by one or more drusen in one or both eyes developing advanced AMD. Since each individual will have two copies of each allele, possible allele combinations at the rs3766405 and rs412852 SNPs include: cytosine (C)/C; C/thymine (T); and T/T. In the example shown in Table 1, risk of an individual with AMD having one or more drusen in one or both eyes developing advanced AMD is determined based on the genotype of the individual at rs3766405 and rs412852.

TABLE 1

| rs3766405 | rs412852 | Risk |
|---|---|---|
| CC | CC | High |
| CT | CT | Medium |
| CC | CT | |
| CC | TT | Low |

TABLE 1-continued

| rs3766405 | rs412852 | Risk |
|---|---|---|
| CT | CC | |
| CT | TT | |
| TT | CC | |
| TT | CT | |
| TT | TT | |

In another embodiment, rs1061170 is used to determine risk of a subject with AMD characterized by having one or more drusen in one or both eyes developing advanced AMD. Since each individual will have two copies of each allele, possible allele combinations at the rs1061170 SNP include: C/C (high risk); C/T (medium risk); and T/T (low risk).

Polymorphic forms of the three SNPs: rs3766405, rs412852 and rs1061170, which are associated with the risk of developing AMD, are shown herein to be associated with accelerated deterioration of vision from AMD in those taking zinc-containing dietary supplements. Without wishing to be bound by theory, it is reasonable to speculate that the same pathophysiological mechanisms associated with AMD disease predisposition account for accelerated vision loss with zinc exposure, since zinc is a naturally containing dietary nutrient. Individuals genetically predisposed to AMD and exposed to dietary zinc get advanced AMD at a higher rate than those without genetic risk factors, or those with low zinc exposure. Treatment with pharmacological doses of zinc (25 mg or greater per day), accelerates the normal progression of AMD. Thus, variations within the CFH gene that predispose to the development of AMD are expected to be associated with increased sensitivity to zinc supplementation, and associated with accelerated progression of this condition. Similarly, individuals without CFH genetic risk factors for AMD development can be expected to have a reduced risk for AMD progression in the presence of zinc. Therefore, in further embodiments, the SNPs shown in Table 2 are also considered to be risk indicators in subjects with AMD. The following SNPs can thus be used to detect a subject at risk of developing advanced AMD, either alone, in combination with each other, and/or with one or more additional single nucleotide polymorphism in the CFH gene.

TABLE 2

| SNP | Risk Allele | SEQ ID NO: |
|---|---|---|
| rs1061170 | C | 3 |
| rs2274700 | G | 4 |
| rs403846 | A | 5 |
| rs12144939 | G | 6 |
| rs1409153 | G | 7 |
| rs1750311 | C | 8 |
| rs10922153 | G | 9 |
| rs698859 | A | 10 |
| rs2990510 | T | 11 |
| rs3753394 | C | 12 |
| rs529825 | C | 13 |
| rs800292 | T | 14 |
| rs3766404 | C | 15 |
| rs1061147 | A | 16 |
| rs2033674 | T | 17 |
| rs3753396 | G | 18 |
| rs1065489 | T | 19 |
| rs1048663 | G | 23 |
| rs11582939 | T | 24 |
| rs1280514 | G | 25 |

In another embodiment, the subject's risk of developing advanced AMD is based on their genetic profile for the Age-Related Maculopathy Susceptibility 2 (ARMS2) gene in addition to the subject' genetic profile at CFH. In one embodiment, the insertion/deletion (indel) polymorphism described in U.S. Pat. No. 8,168,390 (the contents of which is hereby incorporated in its entirety) can be used to determine the subject's risk of developing advanced AMD. In another embodiment, rs10490924 (see FIG. 1V—SEQ ID NO:22), which is in linkage disequilibrium with the indel polymorphism, is used to determine the subject's risk of developing advanced AMD. Since each individual will have two copies of each allele, possible allele combinations at the rs10490924 SNP include: T/T (high risk); G/T (medium risk); and G/G (low risk).

The indel polymorphism resides in the 3'-UTR of the ARMS2 gene and represents a combination of a deletion and insertion (*372_815delins54). The deletion removes the polyadenylation signal sequence at position *395_400 used for the addition of a poly(A) tract 19 bp downstream. The insertion introduces a 54-bp AU-rich element known for its properties to control mRNA decay in many transcripts that encode a wide variety of proteins involved in transient biological processes.

The nucleic acid sequence of the human ARMS2 gene (FIG. 1T, SEQ ID NO. 20) contains a nucleic acid sequence from position 3143 to 3585, which is deleted or removed from the gene in those individuals susceptible to or having AMD. In place of this deleted sequence, a sequence of 54 nucleotides, is inserted into the ARMS2 gene to produce the nucleic acid sequence shown in SEQ ID NO. 21 (FIG. 1U).

A subject is considered to be at low risk of developing advanced AMD if they are homozygous for the wild-type sequence (i.e. either allele does not contain the indel polymorphism). A subject is considered to be at medium risk of developing advanced AMD if they are heterozygous for the indel polymorphism, and at low risk when they are homozygous for the indel polymorphism.

When the subject has 2 high risk alleles at the complement factor H gene and has no high risk ARMS2 risk alleles, then the subject is a candidate for treatment with a vitamin supplement that comprises antioxidants and is free from zinc and/or copper.

When the subject has 2 high risk alleles at the complement factor H gene and has one high risk ARMS2 risk alleles, then the subject is a candidate for treatment with a vitamin supplement that comprises antioxidants and is free from zinc and/or copper.

When the subject has 1 high risk allele at the complement factor H gene and has no high risk ARMS2 risk alleles, then the subject is a candidate for treatment with a vitamin supplement that comprises antioxidants and is free from zinc and/or copper.

When the subject has 1 high risk alleles at the complement factor H gene and has one high risk ARMS2 risk allele, then the subject is a candidate for treatment with a vitamin supplement that comprises antioxidants and zinc and/or copper.

When the subject has no risk complement factor H alleles and has 0 risk alleles for the ARMS2 gene, then the subject is a candidate for treatment with a vitamin supplement that contains zinc and/or copper or contains just antioxidants.

When the subject has no risk complement factor H alleles and has 1 risk alleles for the ARMS2 gene, then the subject is a candidate for treatment with a vitamin supplement that contains zinc and/or copper and no antioxidants. When the subject has no risk complement factor H alleles and has 2 risk alleles for the ARMS2 gene, then the subject is a candidate for treatment with a vitamin supplement that contains zinc and/or copper and no antioxidants.

Numerous methods exist for the measurement of a specific polymorphism or SNP. Individuals carrying polymorphisms at one or more markers in the CFH gene or the indel polymorphism in the ARMS2 gene may be detected at the DNA level by a variety of techniques. Nucleic acids for diagnosis may be obtained from a patient's cells, such as from blood, urine, saliva, tissue biopsy and autopsy material. The nucleic acid sample can be isolated from a biological sample using standard techniques. The nucleic acid sample may be isolated from the subject and then directly utilized in a method for determining the presence of a polymorphic variant, or alternatively, the sample may be isolated and then stored (e.g., frozen) for a period of time before being subjected to analysis.

Genomic DNA may be used directly for detection or may be amplified enzymatically by using PCR prior to analysis (Saiki R K et al., 1986, Nature 324(6093):163-6). As an example, PCR primers complementary to the nucleic acid of one or more polymorphic variants of the present invention, as shown in FIG. 1, can be used to identify and analyze the presence or absence of the polymorphic variant. For example, deletions and insertions can be detected by a change in size of the amplified product in comparison to the normal genotype. Polymorphic forms of the ARMS2 gene, specifically c.*372_815del443ins54 can be identified by hybridizing amplified DNA to radiolabeled RNA of the present invention or alternatively, radiolabeled antisense DNA sequences of the present invention. Perfectly matched sequences can be distinguished from mismatched duplexes by RNase A digestion or by differences in melting temperatures.

Sequence differences between a reference gene and genes having a polymorphism also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with a double-stranded PCR product or a single-stranded template molecule generated by a modified PCR technique. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (Myers R M et al., 1985, Science 230(4731):1242-6).

Sequence changes at specific locations also may be revealed by nuclease protection assays, such as RNase and S1 protection or the chemical cleavage method (Cotton R G et al., 1988, Proc Natl Acad Sci USA 85(12):4397-401).

Thus, the detection of a specific DNA sequence may be achieved by methods which include, but are not limited to, hybridization, chemical cleavage, direct DNA sequencing or the use of restriction enzymes, (e.g., restriction fragment length polymorphisms ("RFLP")) and Southern blotting of genomic DNA. In addition, RNA or mRNA expression levels may be specifically determined by a number of different methods, including, but not limited to nuclease protection assay, Northern blot analysis, in situ hybridization or reverse-transcriptase polymerase chain reaction.

In addition to more conventional gel-electrophoresis and DNA sequencing, mutations also can be detected by in situ analysis.

Furthermore, the presence or absence of the SNP or indel polymorphism can be determined using one or both chromosomal complements represented in the nucleic acid sample. Determining the presence or absence of a polymorphic variant in both chromosomal complements represented in a nucleic acid sample is useful for determining the zygosity of an individual for the polymorphic variant (i.e., whether the individual is homozygous or heterozygous for the polymorphic variant). Any oligonucleotide-based diagnostic may be utilized to determine whether a sample includes the presence or absence of a polymorphic variant in a sample. For example, primer extension methods, ligase sequence determination methods (e.g., U.S. Pat. Nos. 5,679,524 and 5,952,174, and WO 01/27326), mismatch sequence determination methods (e.g., U.S. Pat. Nos. 5,851,770; 5,958,692; 6,110,684; and 6,183,958), microarray sequence determination methods, restriction fragment length polymorphism (RFLP), single strand conformation polymorphism detection (SSCP) (e.g., U.S. Pat. Nos. 5,891,625 and 6,013,499), PCR-based assays (e.g., TAQMAN™ PCR System (Applied Biosystems)), and nucleotide sequencing methods may be used.

Oligonucleotide extension methods typically involve providing a pair of oligonucleotide primers in a polymerase chain reaction (PCR) or in other nucleic acid amplification methods for the purpose of amplifying a region from the nucleic acid sample that comprises the polymorphic variation. One oligonucleotide primer is complementary to a region 3' or downstream of the polymorphism and the other is complementary to a region 5' or upstream of the polymorphism. A PCR primer pair may be used in methods disclosed in U.S. Pat. Nos. 4,683,195; 4,683,202, 4,965,188; 5,656,493; 5,998,143; 6,140,054; WO 01/27327; and WO 01/27329 for example. PCR primer pairs may also be used in any commercially available machines that perform PCR, such as any of the GENEAMP™, systems available from Applied Biosystems. Also, those of ordinary skill in the art will be able to design oligonucleotide primers based upon the nucleotide sequences set forth in SEQ ID NOs:1-25.

Also provided is an extension oligonucleotide that hybridizes to the amplified fragment adjacent to the polymorphic variation. An adjacent fragment refers to the 3' end of the extension oligonucleotide being often 1 nucleotide from the 5' end of the polymorphic site, and sometimes 2, 3, 4, 5, 6, 7, 8, 9, or 10 nucleotides from the 5' end of the polymorphic site, in the nucleic acid when the extension oligonucleotide is hybridized to the nucleic acid. The extension oligonucleotide then is extended by one or more nucleotides, and the number and/or type of nucleotides that are added to the extension oligonucleotide determine whether the polymorphic variant is present. Oligonucleotide extension methods are disclosed, for example, in U.S. Pat. Nos. 4,656,127; 4,851,331; 5,679,524; 5,834,189; 5,876,934; 5,908,755; 5,912,118; 5,976,802; 5,981,186; 6,004,744; 6,013,431; 6,017,702; 6,046,005; 6,087,095; 6,210,891; and WO 01/20039. Oligonucleotide extension methods using mass spectrometry are described, for example, in U.S. Pat. Nos. 5,547,835; 5,605,798; 5,691,141; 5,849,542; 5,869,242; 5,928,906; 6,043,031; and 6,194,144. Multiple extension oligonucleotides may be utilized in one reaction, which is referred to as multiplexing.

Genetic mutations can be identified by hybridizing a sample and control nucleic acids, e.g., DNA or RNA, to high density arrays containing hundreds or thousands of oligonucleotides probes (Cronin M T et al., Hum Mutat 7(3):244-55; Kozal M J et al., 1996, Nat Med 2(7):753-9). For example, genetic mutations can be identified in two-dimensional arrays containing light-generated DNA probes as described in Cronin et al., (supra). Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene. Specific mutations can also be determined through direct sequencing of one or both strands of DNA using dideoxy nucleotide chain termination chemistry, electrophoresis through a semi-solid matrix and fluorescent or radioactive chain length detection techniques. Further mutation detection techniques may involve differential susceptibility of the polymorphic double strand to restriction endonuclease digestion, or altered electrophoretic gel mobility of single or double stranded gene fragments containing one polymorphic form. Other techniques to detect specific DNA polymorphisms or mutation may involve evaluation of the structural characteristics at the site of polymorphism using nuclear magnetic resonance or x-ray diffraction techniques.

An apparatus for detecting a nucleotide in a nucleic acid sequence is also provided. The apparatus comprises a substrate, such as a glass slide, and at least one oligonucleotide bound to the substrate. The oligonucleotide comprising a contiguous nucleic acid sequence complementary to any one of SEQ ID NOs. 1 to 19 and 22-25 and containing position 27 of the sequence, including both the wild-type allele and the polymorphism. In most cases, a second oligonucleotide will be bound to the substrate which corresponds to the oligonucleotide not already bound to the substrate. However, this second sequence could include the wild-type or polymorphic sequence of the sequence already bound to the substrate. In further embodiments, the substrate will contain alone or in combination with SEQ ID NOs: 1, 2 and/or 3, at least an oligonucleotide comprising a contiguous nucleic acid sequence complementary to SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO: 23, SEQ ID NO: 24 and/or SEQ ID NO: 25 and containing position 27 of the sequence.

Although the length of the oligonucleotides for use with the apparatus can be chosen in part based on the overall characteristics of the oligonucleotides on the substrate, a preferred range of lengths are between 25-mer and 60-mer.

A microarray can be utilized for determining whether the polymorphism is present or absent in a nucleic acid sample. A microarray may include any oligonucleotides described hereinabove, and methods for making and using oligonucleotide microarrays suitable for diagnostic use are disclosed in U.S. Pat. Nos. 5,492,806; 5,525,464; 5,589,330; 5,695,940; 5,849,483; 6,018,041; 6,045,996; 6,136,541; 6,142,681; 6,156,501; 6,197,506; 6,223,127; 6,225,625; 6,229,911; 6,239,273; WO 00/52625; WO 01/25485; and WO 01/29259. The microarray typically comprises a solid support and the oligonucleotides may be linked to this solid support by covalent bonds or by non-covalent interactions. The oligonucleotides may also be linked to the solid support directly or by a spacer molecule. A microarray may comprise one or more oligonucleotides complementary to a polymorphism.

Unless otherwise specified, all references cited are incorporated herein.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features herein set forth, and as follows in the scope of the appended claims.

EXAMPLES

Subject Sample

Samples and corresponding genetic and supplement profiles came from the AREDS study. The study procedures have been reported elsewhere (see AREDS report no. 8, Arch Ophthalmol 119:1417-36, 2001).

Subjects used for the present study were classified based on the category of AMD in his or her worse eye. Subjects chosen for observation had AREDS category 3 in one eye and either AREDS categories 1-4 in the fellow eye. The AREDS classification of AMD and definitions are provided below:

I. Definitions:

1. Small drusen. Drusen <63 microns (μM) in diameter located within 2 disc diameters of the center of the macula.
2. Intermediate drusen. Drusen >63 microns but <125 microns in diameter located within 2 disc diameters of the center of the macula.
3. Large drusen. Drusen >125 microns in diameter located within 2 disc diameters of the center of the macula.
4. Advanced AMD. Atrophic or exudative neovascular changes of AMD that include one or more of the following:
   - (a) Definite geographic atrophy definitely or questionably involving the center of the macula (minimum diameter for a patch of atrophy to be classified as geographic is that of circle I1, or 175 cM)
   - (b) Evidence suggesting exudative disease, including:
     - (1) Serous detachment of the sensory retina
     - (2) Subretinal hemorrhage
     - (3) Retinal pigment epithelial detachment (PED) excluding drusenoid type
     - (4) Disciform scar (subretinal fibrous tissue)
     - (5) Scar of previous photocoagulation presumed to have been for treatment of choroidal new vessels (CNV).
     - (6) Retinal pigment epithelial abnormalities consistent with AMD. One or more of the following:
       - (a) retinal pigment epithelial depigmentation definitely present within 1 disc diameter of the center of the macula (i.e., in the center and inner subfields of the standard grid)
       - (b) increased pigmentation of the RPE and/or retina within 1 disc diameter of the center of the macula if its total extent equals or exceeds standard circle C1 (125 microns in diameter)
       - (c) any definite increased RPE pigmentation within 1 disc diameter of the center of the macula if RPE depigmentation is at least questionably present within 1 disc diameter of the center of the macula
       - (d) absence of characteristics suggestive of some condition other than AMD.

II. AMD Classification

1. AMD Category 1. Each eye has:
   - (a) No drusen or small, nonextensive drusen
   - (b) No intermediate drusen
   - (c) No large drusen
   - (d) No pigment abnormalities
   - (e) No advanced AMD
   - (f) A visual acuity score of 74 letters or more
   - (g) No disqualifying lesions.
2. AMD Category 2. At least one eye has one or more intermediate drusen, extensive small drusen, or pigment abnormalities associated with AMD, and neither eye has:
   - (a) Large drusen
   - (b) Advanced AMD
   - (c) A visual acuity score of 73 or less
   - (d) A disqualifying lesion.
3. AMD Category 3. There are two types of AMD Category 3 participants.
   - (a) At least one eye has one or more of the following:
     - (1) One or more large drusen
     - (2) Intermediate drusen, with total drusen area
       - (a) At least that of Circle I-2 (i.e., about 20 average-size intermediate drusen) if soft indistinct drusen are present or
       - (b) At least that of Circle O-2 (i.e., about ⅕ disc area, or about 65 average-size intermediate drusen) if soft indistinct drusen are absent
     - (3) Definite geographic atrophy not involving the center of the macula, and neither eye has any of the following:
4. AMD Category 4. There are two types of AMD Category 4 participants.
   - (a) Eye has advanced AMD with or without visual acuity score of 73 or less,
   - (b) No disqualifying lesion.

Subjects were prescribed oral tablets of placebo, antioxidants, zinc or antioxidants plus zinc. Antioxidants used in this study included 15 mg of β-carotene, 500 mg of vitamin C, and 400 IU of vitamin E. Zinc supplements included 80 mg as zinc oxide and copper. Copper was included to prevent zinc-induced copper-deficiency anemia.

Subjects were examined every 6 months, and stereoscopic fundus photographs were obtained routinely from all eyes at baseline, at the 2-year follow-up visit, and every year thereafter. The average duration of treatment was 6.3 years.

Individuals were considered to have progressed if, from baseline to the end of the study, he or she advanced from AREDS category 3 (intermediate AMD) to category 4 (unilateral advanced AMD) or category 5 (bilateral advanced AMD).

Genotyping

Based on the genotype of the subject at rs3766405 and rs412852, the individual was categorized according to Table 1 as either high, medium or low risk of advancing to AREDS category 4 or 5. Separately, based on the genotype of the subject at rs1061170, the individual was categorized as described above as either high, medium or low risk of advancing to AREDS category 4.

Genotyping was also conducted for the insertion/deletion (indel) polymorphism in the ARMS2 gene. The individual was categorized as either high, medium or low risk of developing advanced AMD depending on whether they were homozygous for the indel polymorphism (high risk), heterozygous for the indel polymorphism (medium risk) or homozygous for the wild type allele (i.e. no insertion/deletion in the ARMS2 gene) (low risk).

Statistical Analysis

Patients (n=995), were divided into 2 groups. The first group (case label "1", n=291 subjects), were observed to progress from AREDS category 3 in one eye and AREDS category 1-4 in the fellow eye, to an incremental AREDS category 4 eye during the period of observation. The second group (case label "0") did not progress. Based on genotyping data and information from the AREDS study data base, each case was classified according to 3 parameters: Treatment category (TRTCAT 1 (placebo alone), 2 (antioxidants alone), 3 (zinc/copper alone) or 4 (antioxidants+zinc/copper)), CFH risk status (High, Medium and Low) based on their genetic profile at rs3766405 and rs412852 and ARMS2 status (High, Medium and Low) based on the presence or absence of the (*372.sub.—815delins54). Patient groups were compared using a cox proportionalte hazards model and statistical significance was determined using the Chi Square statistic. The following chart shows the number of patients in each category.

TABLE 3

| | CFH | | | | ARMS2 | | | |
|---|---|---|---|---|---|---|---|---|
| | LL | LH | HH | P-value | LL | LH | HH | P-value |
| Placebo | 30 | 125 | 78 | 0.479 | 102 | 101 | 30 | 0.877 |
| AO | 31 | 127 | 102 | | 110 | 114 | 36 | |
| Zinc | 35 | 111 | 86 | | 90 | 106 | 36 | |
| AO + Zinc | 30 | 147 | 93 | | 112 | 121 | 37 | |
| Total | 126 | 510 | 359 | 995 | 414 | 442 | 139 | 995 |

Results

As shown in FIG. 2, treatment with zinc+antioxidants did not lower the conversion rate to AREDS category 4 disease. Because of the relatively low rate of conversion, no studied therapy improved upon the performance of placebo-treated patients.

Figure 3:
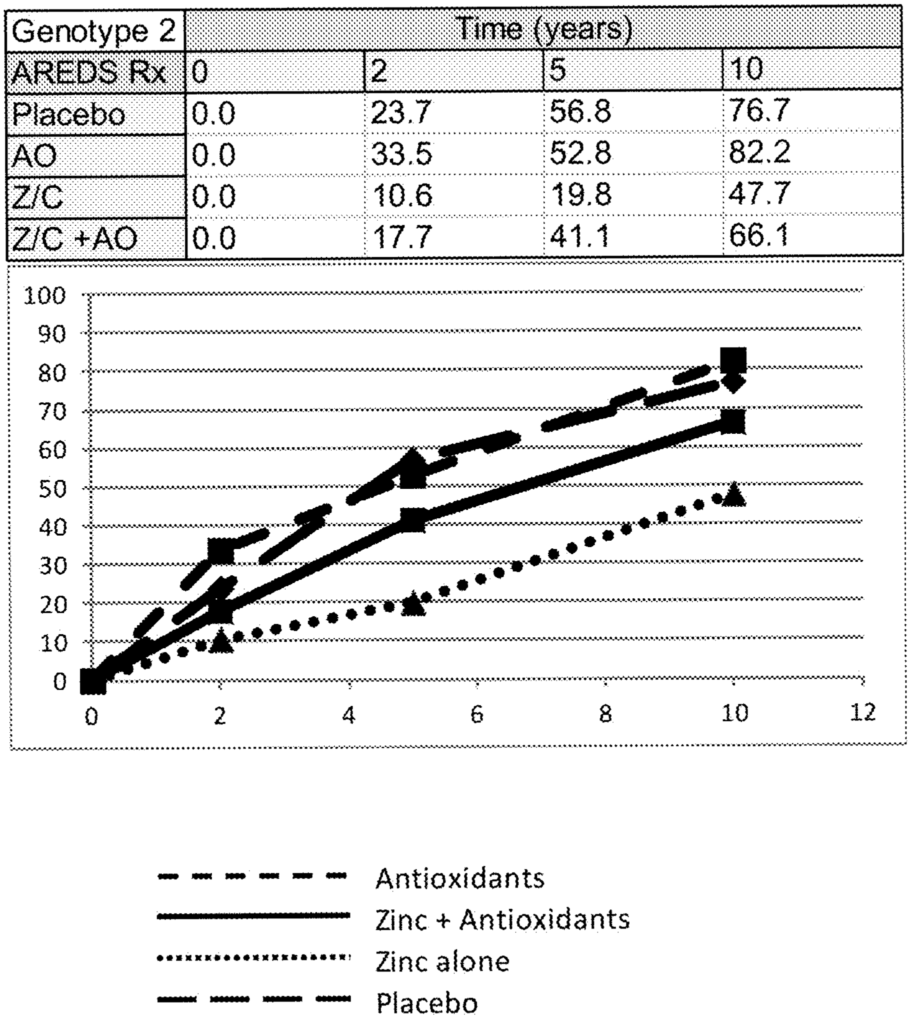
FIG. 3 is a graphical representation of the percentage of subjects having no CFH and one ARMS2 risk alleles estimated to progress from AREDS category 3 disease in at least one eye to AREDS category 4 disease in the eye that initially had category 3 disease. The graph shows the variable "Time" on the X axis and "Percent Progressing" on the Y axis.
Figure 4:
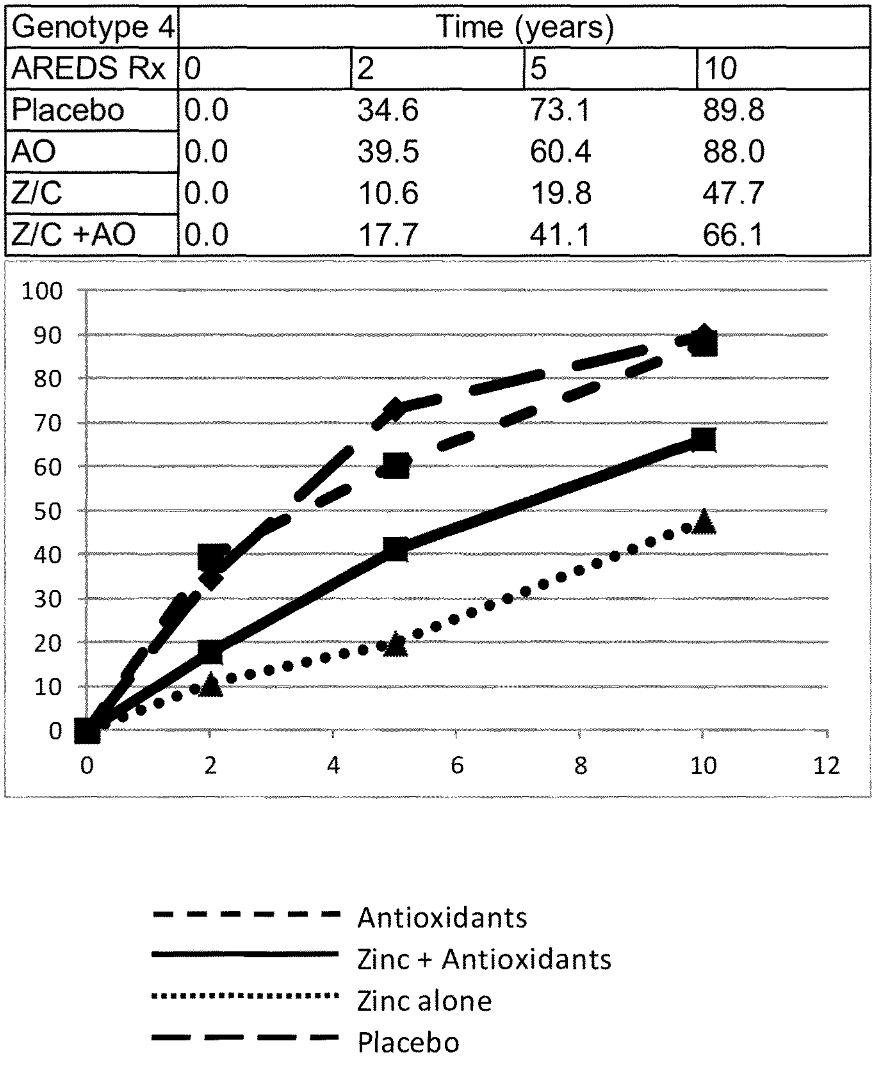
FIG. 4 is a graphical representation of the percentage of subjects having no CFH and two ARMS2 risk alleles estimated to progress from AREDS category 3 disease in at least one eye to AREDS category 4 disease in the eye that initially had category 3 disease. The graph shows the variable "Time" on the X axis and "Percent Progressing" on the Y axis.
Figure 5:
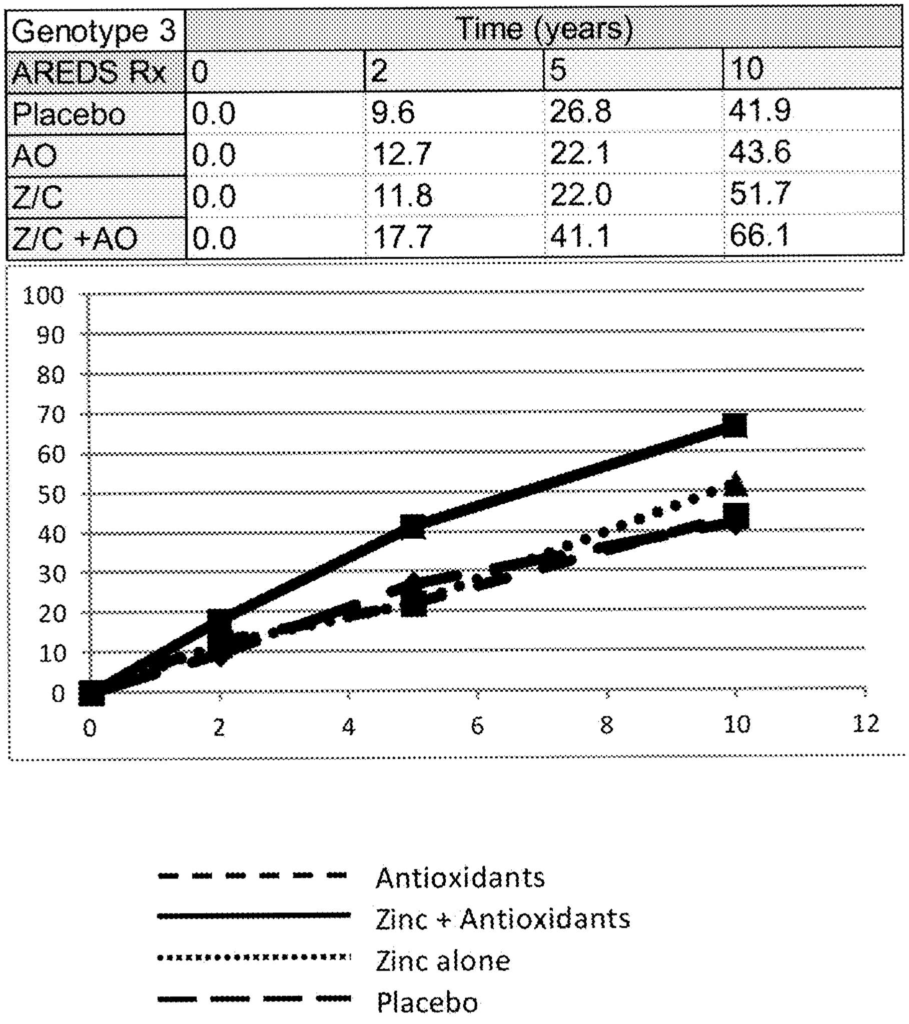
FIG. 5 is a graphical representation of the percentage of subjects having one CFH and no ARMS2 risk alleles estimated to progress from AREDS category 3 disease in at least one eye to AREDS category 4 disease in the eye that initially had category 3 disease. The graph shows the variable "Time" on the X axis and "Percent Progressing" on the Y axis.

As shown in FIGS. 3 and 4, individuals with no CFH risk alleles and one or 2 ARMS2 risk allele behave differently from those with no risk alleles. In this group treatment with antioxidants does not appear to have any value, rather the maximal benefit occurs with the administration of zinc/copper alone. The addition of antioxidants to zinc reduces the therapeutic effect, reflecting the negative interaction of ARMS2 risk alleles and antioxidant administration.

Figure 6:
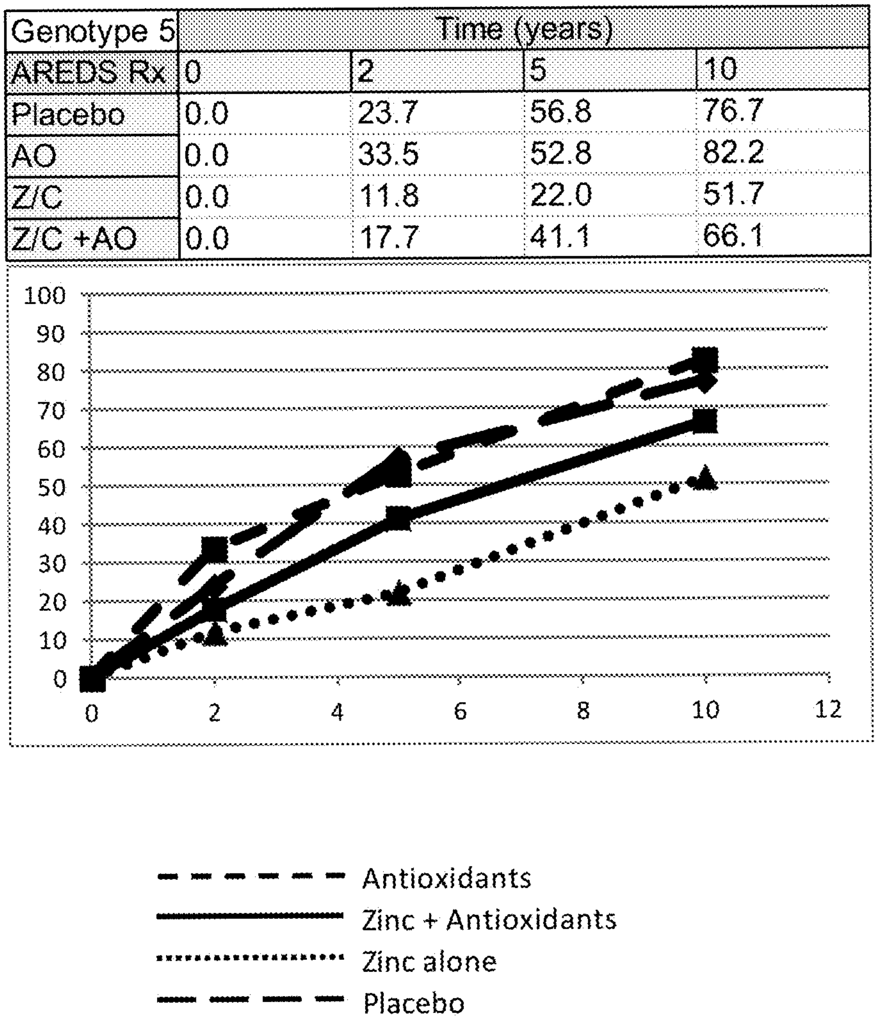
FIG. 6 is a graphical representation of the percentage of subjects having one CFH and one ARMS2 risk alleles estimated to progress from AREDS category 3 disease in at least one eye to AREDS category 4 disease in the eye that initially had category 3 disease. The graph shows the variable "Time" on the X axis and "Percent Progressing" on the Y axis.

As shown in FIG. 6 individuals with 1 CFH risk allele and 1 or 2 ARMS2 risk alleles benefit maximally from the administration of antioxidants combined with zinc/copper alone.

Figure 7:
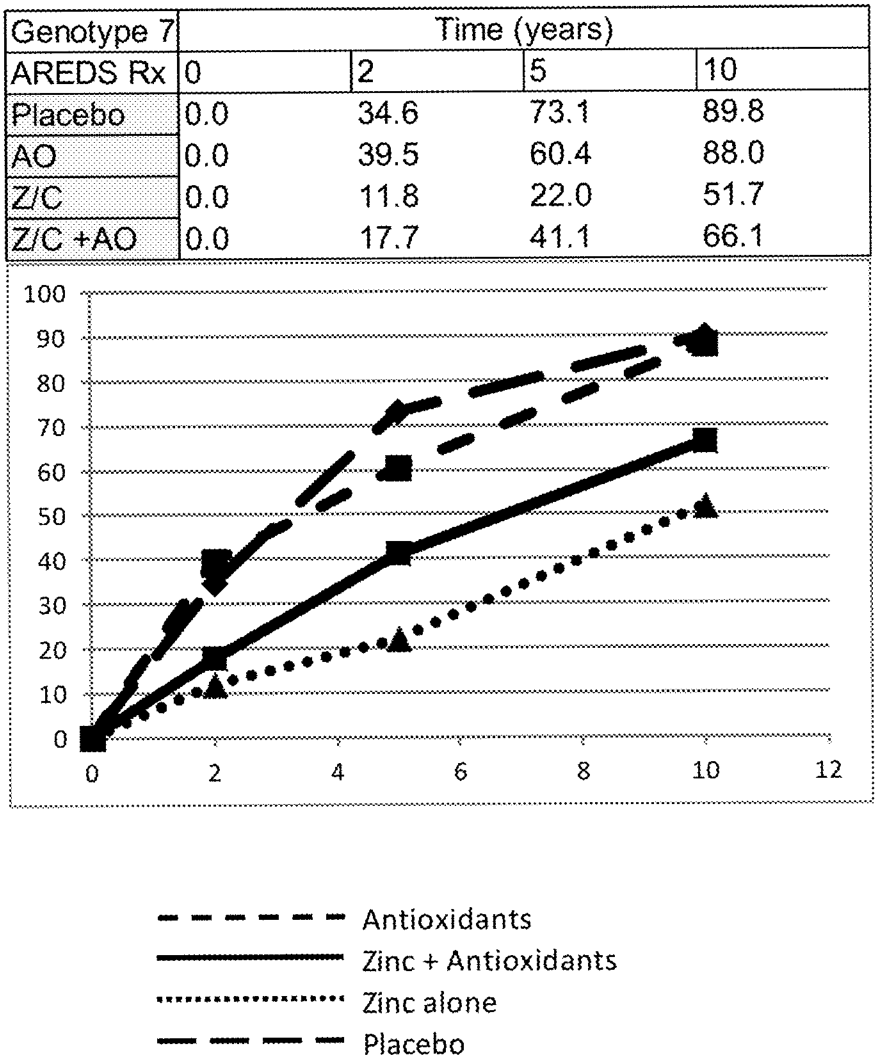
FIG. 7 is a graphical representation of the percentage of subjects having one CFH and two ARMS2 risk alleles estimated to progress from AREDS category 3 disease in at least one eye to AREDS category 4 disease in the eye that initially had category 3 disease. The graph shows the variable "Time" on the X axis and "Percent Progressing" on the Y axis.

As shown in FIG. 7 individuals with 1 CFH risk allele and 2 ARMS2 risk alleles benefit maximally from the administration of zinc/copper and should avoid antioxidants.

Figure 8:
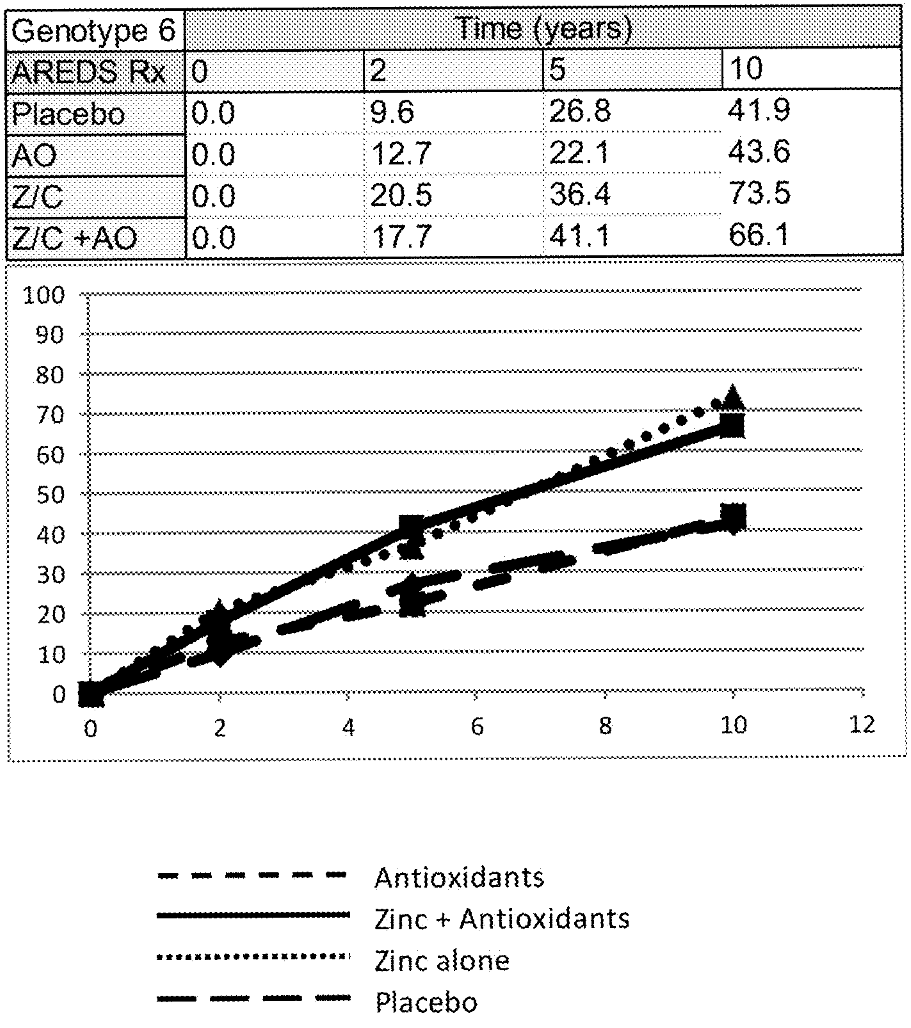
FIG. 8 is a graphical representation of the percentage of subjects having two CFH and no ARMS2 risk alleles estimated to progress from AREDS category 3 disease in at least one eye to AREDS category 4 disease in the eye that initially had category 3 disease. The graph shows the variable "Time" on the X axis and "Percent Progressing" on the Y axis.

As shown in FIG. 8, individuals with 2 CFH risk alleles and no ARMS2 risk alleles experience a negative effect with the administration of zinc. These individuals do worse with the administration of zinc/copper+antioxidants than with antioxidants alone. In this group zinc should be avoided.

Figure 9:
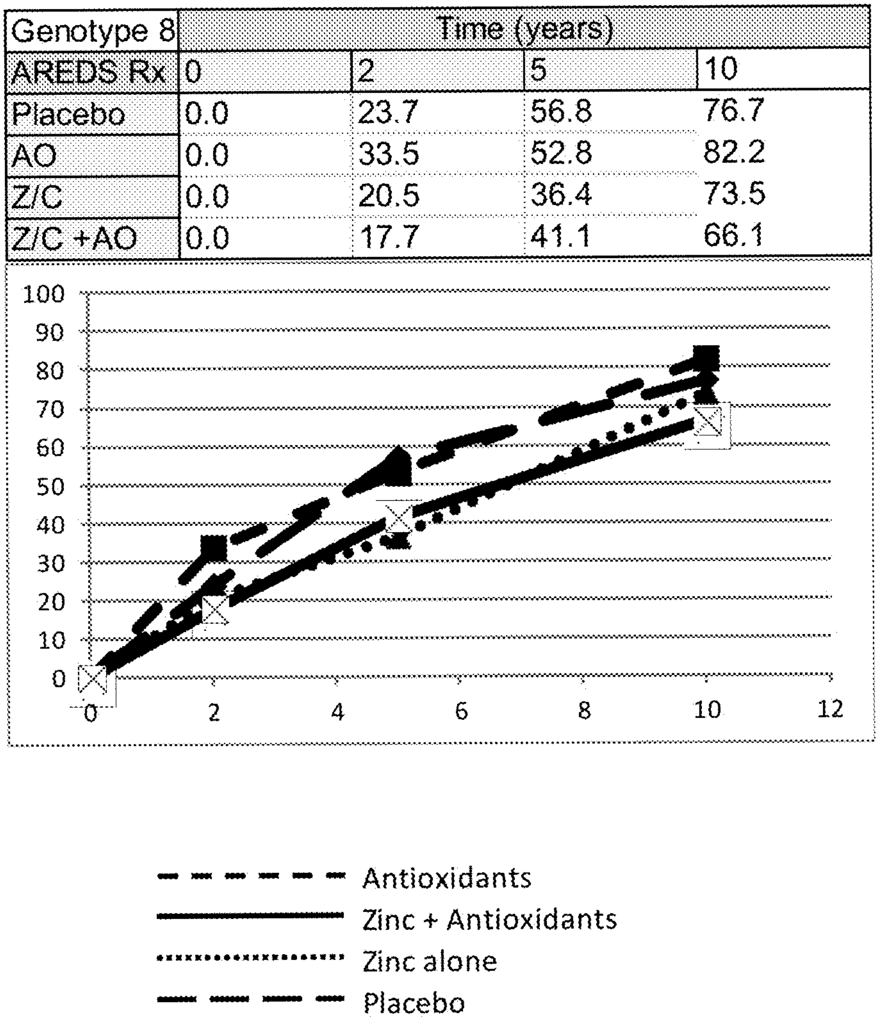
FIG. 9 is a graphical representation of the percentage of subjects having two CFH and one ARMS2 risk alleles estimated to progress from AREDS category 3 disease in at least one eye to AREDS category 4 disease in the eye that initially had category 3 disease. The graph shows the variable "Time" on the X axis and "Percent Progressing" on the Y axis.
Figure 10:
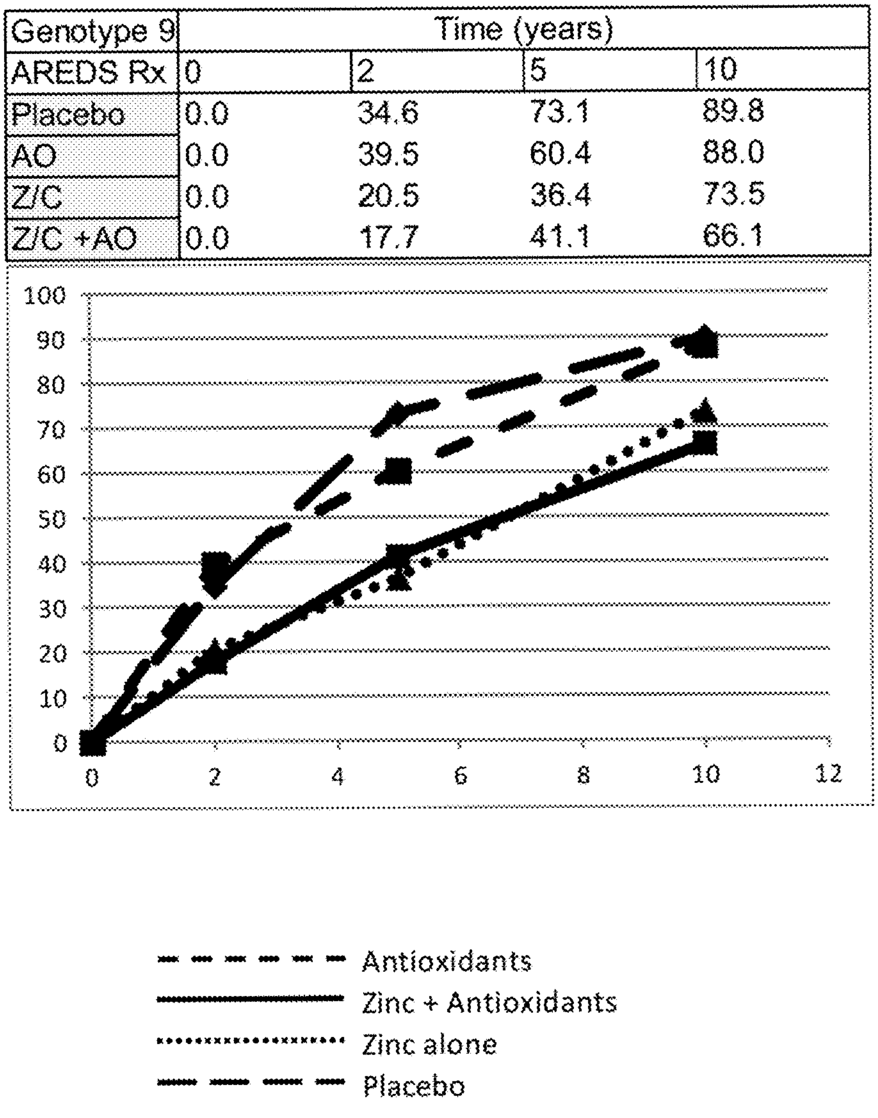
FIG. 10 is a graphical representation of the percentage of subjects having two CFH and two ARMS2 risk alleles estimated to progress from AREDS category 3 disease in at least one eye to AREDS category 4 disease in the eye that initially had category 3 disease. The graph shows the variable "Time" on the X axis and "Percent Progressing" on the Y axis.

As shown in FIGS. 9 and 10, individuals with 2 CFH risk alleles and 1 or 2 ARMS2 risk alleles are best treated with a combination of zinc/copper or antioxidants. Antioxidants with zinc/copper alone are inferior to placebo and may be deleterious due to the negative interaction of both risk factors and this combined treatment.

Figure 11:
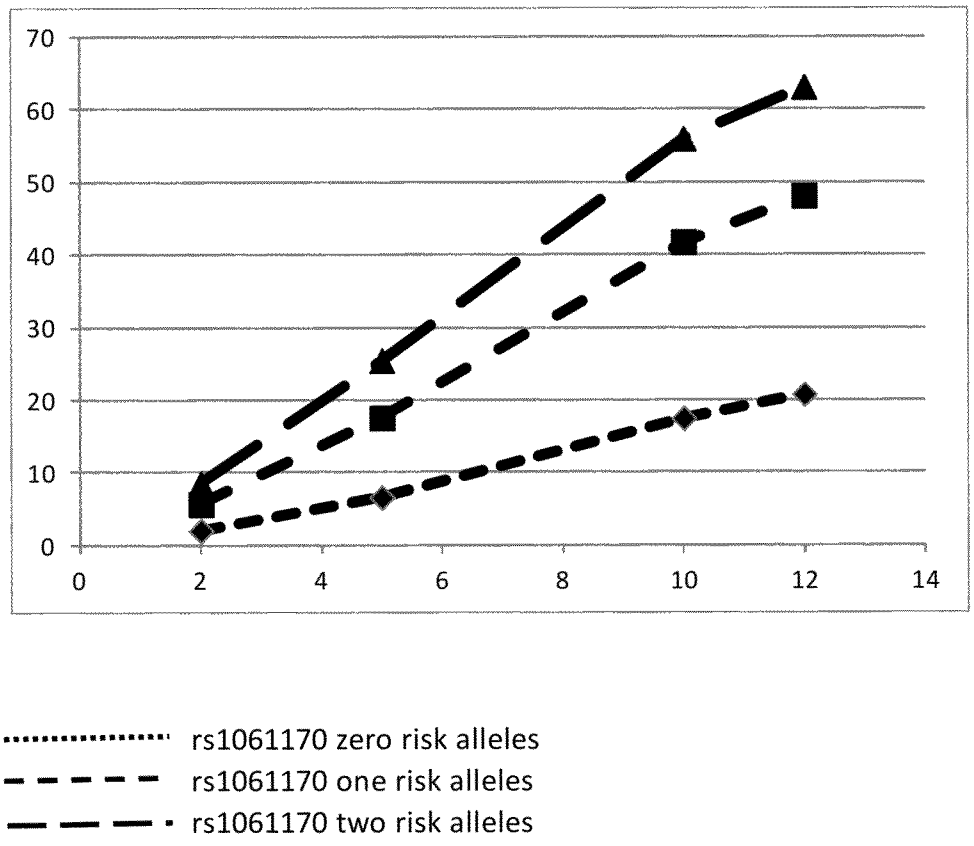
FIG. 11 is a graphical representation of the percentage of subjects having zero, one or two rs1061170 CFH risk alleles estimated to progress from AREDS category 3 disease in at least one eye to AREDS category 4 disease in the eye that initially had category 3 disease. The graph shows the variable "Time" on the X axis and "Percent Progressing" on the Y axis.

As shown in FIG. 11 a similar interaction between CFH risk, as measured using the rs1066170 single SNP in the CFH gene, and zinc administration is demonstrated. Individuals receiving zinc/copper experience over 60% progression to advanced disease by 12 years of follow-up. Those with 1 risk allele have 50% progression by 12 years, while those with no risk alleles have only 20% progression risk.

In summary, those subjects having a low risk genetic profile, as described above, benefitted from antioxidant and zinc treatment in that this supplement regime could prolong or prevent disease progression to advanced AMD. In those high risk subjects, treatment with antioxidants and/or zinc negatively impacted the individual by contributing to a more rapid disease progression compared to the same risk group prescribed placebo.

When the genetic profile of an individual at rs1061170 was used as the marker to determine whether the individual was at high, medium or low risk of progressing to advanced AMD, it was shown that those individuals classified as being at high risk were negatively impacted by treatment with zinc, whereas those considered at low risk benefitted from this treatment (FIG. 11). Individuals at medium risk of developing advanced AMD treated with zinc were at risk intermediate between those at high risk and those at low risk at having the disease progress to advanced AMD (FIG. 11).

To evaluate the interaction of the CFH and the ARMS2 polymorphisms identified by treatment group-specific forward stepwise regression, cox proportional hazards regression using each of the covariants: TRTCAT1 (placebo); TRTCAT2 (antioxidants—β-carotene, (Table 4). For this analysis a co-dominance of each marker with individual patients coded to have 0, 1 or 2 risk alleles (i.e. low, medium or high risk) was assumed. Statistical significance was determined using the chi square test with appropriate degrees of freedom. In consideration of the parallel consideration of data from each of 4 treatment groups the statistical significance threshold was adjusted using the Bonferroni correction (threshold=α/n).

TABLE 4

(a)

| placebo | | Sample Size 235 | |
|---|---|---|---|
| Covariate | Beta | p-level (4 df) | Risk Ratio |
| CFH 1 allele | 0.806 | 0.032 | 2.239 |
| CFH 2 alleles | 0.655 | 0.095 | 1.926 |
| ARMS2 1 allele | 0.562 | 0.010 | 1.754 |
| ARMS2 2 alleles | 1.172 | 0.000 | 3.230 |
| Antioxidants | | Sample Size 256 | |
| Covariate | Beta | p-level (2 df) | Risk Ratio |
| ARMS2 1 allele | 0.948 | 5.749E−05 | 2.581 |
| ARMS2 2 alleles | 1.377 | 2.219E−06 | 3.963 |

TABLE 4-continued (a)

| Zinc | | Sample size 232 | |
|---|---|---|---|
| Covariate | Beta | p-level (2 df) | Risk Ratio |
| CFH 1 allele | 0.781 | 4.161E−02 | 2.184 |
| CFH 2 alleles | 1.495 | 7.522E−05 | 4.461 |
| **Antioxidants + Zinc** | | **Sample Size 272** | |
| Covariate | Beta | p-level (2 df) | Risk Ratio |
| CFH 2 alleles | 0.606 | 1.026E−02 | 1.833 |
| ARMS2 2 alleles | 0.635 | 8.540E−04 | 1.887 |

For individuals receiving placebo both 1 copy of CFH risk allele, 2 copies of the CFH risk allele, 1 copy of the ARMS2 risk allele and 2 copies of the ARMS2 risk allele predicted progression. In contrast, among those patients treated with antioxidants alone the ARMS2 covariant was a significant predictor of risk at the 2.219E-6 level of statistical significance for 2 risk alleles and at the 5.75E-5 for 1 risk allele with overall risk ratios of 3.96 and 2.58 respectively. No other marker was significantly associated with progression risk among antioxidant treated patients. For individuals treated with zinc alone the CFH risk marker was a significant predictor of progression with a risk ratio for zinc-treated individuals. One CFH risk allele produced a risk ratio of 2.18 (p=4.16E-2) and 2 CFH risk alleles produced a risk ratio of 4.46 (p=7.52E-5). For individuals treated with both zinc/copper and antioxidants both CFH and ARMS2 homozygous risk markers predicted progression. For individuals with 2 risk copies of CFH risk alleles, the risk ratio was 1.83 (p=1.03E-2) and for those with 2 risk copies of the ARMS2 allele the risk ratio was 1.89 (p=8.54E-4). Overall, the 2 strongest genetic predictors of AMD progression risk, CFH and ARMS2, were the only statistically significant treatment-specific markers of progression risk, with ARMS2 significantly interacting in antioxidant treated patients and CFH interacting with zinc-containing regimens. In keeping with the additive nature of the effect of AMD risk alleles, it was discovered in each case that a higher risk ratio for transformation in the presence of 2 alleles compared to one.

To further study interaction between CFH risk alleles and zinc therapy, the significance of interaction between treatment group and risk allele number was determined for patients with AREDS category 3 disease at the time of treatment initiation. Patients treated with placebo or zinc+antioxidants had an alpha value of 0.0562 for interaction (Chi Square). A comparison between placebo-treated patients and those treated with zinc alone had a somewhat more significant alpha value of 0.0397 consistent with a role for zinc as a promoter of AMD conversion in the presence of CFH risk alleles. Similarly, an interaction between treatment effect and ARMS2 risk alleles for placebo-treated and anti-oxidant treated patients was evaluated. The alpha value for interaction was 0.0597, a value approaching significance (Table 6).

TABLE 6

(a)

| Effect | DF | Chi-Square (Wald) | Pr > ChiSq |
|---|---|---|---|
| Treatment 1 and 4 and CFH interaction | | | |
| Treatment 1 or 4 | 1 | 2.95 | 0.0858 |
| CFH Risk Alleles | 1 | 0.191 | 0.6618 |
| CFH Risk Alleles and Treatment interaction | 1 | 3.65 | 0.0562 |
| Treatment 1 and 3 and CFH interaction | | | |
| Treatment 1 or 3 | 1 | 2.35 | 0.126 |
| CFH Risk Alleles | 1 | 0.21 | 0.647 |
| CFH Risk Alleles and Treatment interaction | 1 | 4.23 | 0.0397 |
| Treatment 1 and 2 and ARMS2 Interaction | | | |
| Treatment 1 or 3 | 1 | 6.88 | 0.0087 |
| CFH Risk Alleles | 1 | 0.063 | 0.8019 |
| CFH Risk Alleles and Treatment interaction | 1 | 3.54 | 0.0597 |

To generate the data represented in FIGS. 2 to 11, the risk of progression as a function of ARMS2 and CFH genotype in placebo-treated individuals, ARMS2 genotype in antioxidant treated patients, CFH genotype in zinc treated patients and CFH or ARMS2 genotypes in patients treated with both zinc/copper and antioxidants was determined by comparing the cox regression beta values of covariates (Table 4) to the mean of covariates of each treatment group was determined. Using the observed baseline survivor function (at mean of covariates) the progression risk associated with specific genotypes was determined. Nine genotype combinations of ARMS2 and CFH risk alleles were defined (Table 7) and determined the 5, 10 and 12 year conversion rate as a function of assigned treatment group (FIGS. 2-11)

ARMS 2 genotypes were used to determine absolute progression risk among those treated with antioxidants and CFH genotypes to determine absolute progression risk for those treated with zinc alone. ARMS2 and CFH were used to determine the absolute risk of progression for those treated with zinc+antioxidants. While certain combinations of genotypes (1, 8 and 9) were associated with similar progression risk among all 4 treatment groups, others were associated with marked differences in progression as a function of treatment group. For instance, genotype groups 2, 4 and 7 were associated with lower conversion rates with zinc containing regiments than with any other regimen. Genotypes groups 3, 6 and 8 derived no benefit from zinc containing regimens actually doing significantly worse than placebo-treated patients. Genotype groups 3 and 6 derive greater benefit from antioxidants alone than from antioxidants combined with zinc/copper. ARMS 2 alleles seem to decrease the effectiveness of anti-oxidant only therapy in an allele dose dependent fashion. 5 treatment groups were identified that derive greater benefit from either zinc/copper alone or antioxidants alone than from the combination of zinc and antioxidants. There are shown in Table 8 below. Approximately 50 percent of all people with intermediate AMD would get more benefit from genotype-directed therapy than from the universal administration of zinc plus antioxidants. The frequency of each of the genotype combinations is shown (Table 8). Table 9 shows the overall beneficial effect for each genotype combination if treated with the genotype-directed optimal therapy rather than with both zinc and antioxidants. The progression to advance AMD at 10 years improvement is shown and ranges in each group from 6.8 to 28.1 absolute difference in progression proportion.

TABLE 7

| Risk Markers | | CFH 0 | CFH 1 | CFH 2 |
|---|---|---|---|---|
| ARMS2 | 0 | 1 | 3 | 6 |
| | 1 | 2 | 5 | 8 |
| | 2 | 4 | 7 | 9 |

TABLE 8

| Risk Alleles CFH | Risk Alleles ARMS2 | Best AREDS Assigned Treatment* | Study Population Frequency |
|---|---|---|---|
| 0 | 0 | — | 5.86 |
| 0 | 1 | Zinc | 5.26 |
| 1 | 0 | AO | 22.5 |
| 0 | 2 | Zinc | 1.01 |
| 1 | 1 | AO + Zinc | 22.6 |
| 2 | 0 | AO | 13.3 |

TABLE 8-continued

| Risk Alleles CFH | Risk Alleles ARMS2 | Best AREDS Assigned Treatment* | Study Population Frequency |
|---|---|---|---|
| 1 | 2 | Zinc | 6.57 |
| 2 | 1 | — | 16.4 |
| 2 | 2 | — | 6.67 |

TABLE 9

| Marker* CFH | Marker* ARMS2 | Antioxidants + Zinc 5 yrs | Antioxidants + Zinc 10 yrs | Antioxidants alone 5 yrs | Antioxidants alone 10 yrs | Zinc alone 5 yrs | Zinc alone 10 yrs | Progression difference at 10 Yrs (%) |
|---|---|---|---|---|---|---|---|---|
| 2 | 0 | 29.9 | 49.8 | 11.7 | 21.7 | 33.6 | 67.1 | 28.1 |
| 0 | 2 | 29.1 | 48.8 | 38.0 | 62.1 | 8.76 | 22.1 | 26.7 |
| 1 | 0 | 17.1 | 30.6 | 11.4 | 21.7 | 18.2 | 42.0 | 8.90 |
| 0 | 1 | 17.1 | 30.6 | 26.7 | 46.9 | 8.76 | 22.1 | 8.52 |
| 1 | 2 | 29.1 | 48.8 | 38.0 | 62.1 | 18.2 | 42.0 | 6.80 |

The invention claimed is:

1. A method of treating a subject diagnosed with age-related macular degeneration (AMD) and comprising at least one risk allele in the complement factor H (CFH) gene or Age-Related Maculopathy Susceptibility 2 (ARMS2) gene comprising:

(a) determining the subject's risk of developing advanced AMD based on their genetic profile for the complement factor H (CFH) gene and the Age-Related Maculopathy Susceptibility 2 (ARMS2) gene, wherein the subject has i) zero risk alleles for CFH and 1 risk allele for ARMS2, ii) 1 risk allele for CFH and zero risk alleles for ARMS2, iii) 0 risk alleles for CFH and two risk alleles for ARMS2, iv) 2 risk alleles for CFH and zero risk alleles for ARMS2, or v) one risk allele for the CFH gene and two risk alleles for ARMS2, and (b) administering a supplement comprising zinc/copper or antioxidants, but not both, based on the subject's risk determined in (a), wherein when the subject has zero risk alleles for CFH and 1 risk allele for ARMS2 the supplement comprises zinc/copper and is free from antioxidants;

wherein when the subject has 1 risk allele for CFH and zero risk alleles for ARMS2 the supplement comprises antioxidants and is free from zinc and copper;

wherein when the subject has 0 risk alleles for CFH and two risk alleles for ARMS2 the supplement comprises zinc/copper and is free from antioxidants, wherein when the subject has 2 risk alleles for CFH and zero risk alleles for ARMS2 the supplement comprises antioxidants and is free from zinc and copper, wherein when the subject has one risk allele for the CFH gene and two risk alleles at the ARMS2 locus the supplement comprises zinc/copper and is free from antioxidants, wherein the risk allele for CFH is the C allele of single nucleotide polymorphism SNP rs3766405 (SEQ ID NO: 1) and the risk allele for ARMS2 is polymorphism 372 815delins54 in the ARMS2 gene.

2. The method of claim 1, wherein the subject diagnosed with age related macular degeneration has one or more retinal drusen.

3. The method of claim 1, wherein the supplement is in the form of a multi-vitamin.

4. A method of treating a subject diagnosed with age-related macular degeneration (AMD) and comprising at least one risk allele in the complement factor H (CFH) gene or Age-Related Maculopathy Susceptibility 2 (ARMS2) gene comprising:

(a) isolating a DNA sample from a subject and detecting the presence of one or more risk alleles in the complement factor H (CFH) gene and/or the Age-Related Maculopathy Susceptibility 2 (ARMS2) gene in the isolated DNA sample, wherein the detecting comprises:

(i) detecting in the isolated DNA sample the presence or absence of one or two copies of a risk allele in the CFH gene, wherein the risk allele is the C allele of single nucleotide polymorphism SNP rs3766405 (SEQ ID NO: 1); and (ii) detecting in the isolated DNA sample the presence or absence of one or two copies of a risk allele in the ARMS2 gene, wherein the risk allele is polymorphism 372 815delins54;

(b) determining the subject's risk of developing advanced AMD based on their genetic profile for the complement factor H (CFH) gene and the Age-Related Maculopathy Susceptibility 2 (ARMS2) gene and (c) administering a supplement based on the subject's risk determined in (b), wherein:

(i) when the subject has zero risk alleles for CFH and 1 risk allele for ARMS2 the supplement comprises zinc and/or copper and is free from antioxidants;

(ii) when the subject has 1 risk allele for CFH and zero risk alleles for ARMS2 the supplement comprises antioxidants and is free from zinc and copper;

(iii) when the subject has 0 risk alleles for CFH and two risk alleles for ARMS2 the supplement comprises zinc and/or copper and is free from antioxidants, (iv) when the subject has 2 risk alleles for CFH and zero risk alleles for ARMS2 the supplement comprises antioxidants and is free from zinc and copper, (v) when the subject has one risk allele for the CFH gene and two risk alleles for ARMS2 the supplement comprises zinc and/or copper and is free from antioxidants, (vi) when the subject has one risk allele for the CFH gene and one risk allele for ARMS2, the supplement comprises zinc and/or copper, and also comprises antioxidants, and (vii) when the subject has two risk alleles for the CFH gene and one or two risk alleles for ARMS2, the supplement comprises antioxidants and optionally zinc and/or copper.

5. The method of claim 4, wherein the subject diagnosed with age related macular degeneration has one or more retinal drusen.

6. The method of claim 4, wherein the supplement is in the form of a multi-vitamin.

* * * * *

SEQUENCE LISTING

<160> NUMBER OF SEQ ID NOS: 25

<210> SEQ ID NO 1
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: n is c or t
<220> FEATURE:
<221> NAME/KEY: misc_feature
<222> LOCATION: (27)..(27)
<223> OTHER INFORMATION: SNP identification no. rs3766405

<400> SEQUENCE: 1
ctggacattt tatatagtgt gggctgnaac ttaagtttca ccgggtgtgt ct 52

<210> SEQ ID NO 2
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: SNP identification no. rs412852
<220> FEATURE:
<221> NAME/KEY: misc_feature
<222> LOCATION: (27)..(27)
<223> OTHER INFORMATION: n is c or t

<400> SEQUENCE: 2
agaaaccagt tcaaagcctc ctgcaanccc ctaaagtaaa cagagaccaa ta 52

<210> SEQ ID NO 3
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: SNP identification no. rs1061170

<220> FEATURE:
<221> NAME/KEY: misc_feature
<222> LOCATION: (27)..(27)
<223> OTHER INFORMATION: n is c or t

<400> SEQUENCE: 3
atttggaaaa tggatataat caaaatnatg gaagaaagtt tgtacagggt aa 52

<210> SEQ ID NO 4
<211> LENGTH: 51
<212> TYPE: DNA
<213> ORGANISM: Homo sapiens
<220> FEATURE:
<221> NAME/KEY: misc_feature
<222> LOCATION: (27)..(27)
<223> OTHER INFORMATION: SNP identification no. rs2274700
<220> FEATURE:
<221> NAME/KEY: misc_feature
<222> LOCATION: (27)..(27)
<223> OTHER INFORMATION: n is a, c, g or t

<400> SEQUENCE: 4
acatatccta gtttgcattg atatttngct ttttctttta aggcatatgt a 51

<210> SEQ ID NO 5
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: SNP identification no. rs403846
<220> FEATURE:
<221> NAME/KEY: misc_feature
<222> LOCATION: (27)..(27)
<223> OTHER INFORMATION: n is a or g

<400> SEQUENCE: 5
ctttgcttct cagtgcctaa aaaggantac catacaataa caataatatt ta 52

<210> SEQ ID NO 6
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: SNP identification no. rs12144939
<220> FEATURE:
<221> NAME/KEY: misc_feature
<222> LOCATION: (27)..(27)
<223> OTHER INFORMATION: n is a, g or t

<400> SEQUENCE: 6
tttctatttc ctctgaatta atcgtcntag gctgtgtgtc tagaaattta tc 52

<210> SEQ ID NO 7
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: SNP identificatoin no. rs1409153
<220> FEATURE:
<221> NAME/KEY: misc_feature
<222> LOCATION: (27)..(27)
<223> OTHER INFORMATION: n is a or g

<400> SEQUENCE: 7
cataaaatga ttaaaaggta gattagnaac atgaatttga tcaaaatagt at 52

<210> SEQ ID NO 8
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: SNP identification no. rs1750311
<220> FEATURE:
<221> NAME/KEY: misc_feature
<222> LOCATION: (27)..(27)
<223> OTHER INFORMATION: n is a or c

<400> SEQUENCE: 8
tttctaaatt ttttttcagt gggatgntat gttgatagca gctactccat cc 52

<210> SEQ ID NO 9
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: SNP identification no. rs10922153
<220> FEATURE:
<221> NAME/KEY: misc_feature
<222> LOCATION: (27)..(27)
<223> OTHER INFORMATION: n is g or t

<400> SEQUENCE: 9
tttgaaactt tctgaattaa cgttatntaa aaggaaatgt agatgttatt tt 52

<210> SEQ ID NO 10
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: SNP identification no. rs698859
<220> FEATURE:
<221> NAME/KEY: misc_feature
<222> LOCATION: (27)..(27)
<223> OTHER INFORMATION: n is a or g

<400> SEQUENCE: 10
tctaaattat ttgtgctgaa catttcntta tttataaatg aaaaccaata aa 52

<210> SEQ ID NO 11
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: SNP identification no. rs2990510
<220> FEATURE:
<221> NAME/KEY: misc_feature
<222> LOCATION: (27)..(27)
<223> OTHER INFORMATION: n is g or t

<400> SEQUENCE: 11
taagtagagc aatgctttac agtgttngtt gttgagtgct cacaagaagg tg 52

<210> SEQ ID NO 12
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: SNP identification no. rs3753394
<220> FEATURE:
<221> NAME/KEY: misc_feature
<222> LOCATION: (27)..(27)
<223> OTHER INFORMATION: n is c or t

<400> SEQUENCE: 12
aagggtttat gaaatccaga ggatatnacc agctgctgat ttgcacatac ca 52

<210> SEQ ID NO 13
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: SNP identification no. rs529825
<220> FEATURE:
<221> NAME/KEY: misc_feature
<222> LOCATION: (27)..(27)
<223> OTHER INFORMATION: n is c or t

<400> SEQUENCE: 13
gtaaccttgg caatgggtaa gtctatngta ctgtgtaaac ttggactacc tc 52

<210> SEQ ID NO 14
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: SNP identification no. rs800292
<220> FEATURE:
<221> NAME/KEY: misc_feature
<222> LOCATION: (27)..(27)
<223> OTHER INFORMATION: n is c or t

<400> SEQUENCE: 14
ttctcccttc ctgcatacca ttattanatt tccaagagat ctatatccag gg 52

<210> SEQ ID NO 15
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: SNP identification no. rs3766404
<220> FEATURE:
<221> NAME/KEY: misc_feature
<222> LOCATION: (27)..(27)
<223> OTHER INFORMATION: n is c or t

<400> SEQUENCE: 15
aagaaaaaag gaatacattt aggactnatt tgaagttagt gtcaacatca aa 52

<210> SEQ ID NO 16
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: SNP identification no. rs1061147
<220> FEATURE:
<221> NAME/KEY: misc_feature
<222> LOCATION: (27)..(27)

-continued

<223> OTHER INFORMATION: n is a or c

<400> SEQUENCE: 16
tatcctgcaa cccggggaaa tacagcnaaa tgcacaagta ctggctggat ac 52

<210> SEQ ID NO 17
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: SNP identication no. rs2033674
<220> FEATURE:
<221> NAME/KEY: misc_feature
<222> LOCATION: (27)..(27)
<223> OTHER INFORMATION: n is g or t

<400> SEQUENCE: 17
acacaccata ccttggttac atacaantca tattttatca tatttttagt aa 52

<210> SEQ ID NO 18
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: SNP identification no. rs3753396
<220> FEATURE:
<221> NAME/KEY: misc_feature
<222> LOCATION: (27)..(27)
<223> OTHER INFORMATION: n is a or g

<400> SEQUENCE: 18
ctaatgaagg gacctaataa aattcantgt gttgatggag agtggacaac tt 52

<210> SEQ ID NO 19
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: SNP identification no. rs1065489
<220> FEATURE:
<221> NAME/KEY: misc_feature
<222> LOCATION: (27)..(27)
<223> OTHER INFORMATION: n is g or t

<400> SEQUENCE: 19
ggccttcctt gtaaatctcc acctganatt tctcatggtg ttgtagctca ca 52

<210> SEQ ID NO 20
<211> LENGTH: 3690
<212> TYPE: DNA
<213> ORGANISM: Homo sapiens

<400> SEQUENCE: 20
acaaaaaaac aacaaaaaat cccaaaaccc ccaaaactct cattgaccct tatctcagat 60
ttcccgaatg cttaccaccc tcgctacatc attcaagttc ttggaaacat ttaaagcatg 120
tgaaacattt aaaacattta agttggaggc tttaagttgc acgtccttta tttctaaata 180
tttcagtgtg tttttcttaa aaaaaatttt ctcataccac agtaacatga tcaaaattgg 240
aaaatcaaca ttgattcaat actatgatct acaatcaagg tttttttttt ttttcaaatc 300
cctgggtctc tgcatttttt aaaagcttca cagatgattt caatggatac tagggacctc 360

-continued

```
tgttgcctcc tctggcagag caggactgag gggtggaccc tccctgagac cacccaacaa    420
ttcagggtgg agttatcagg gcgccctgac tcctgggggc atttttgtgt gacgggaaaa    480
gacaatgctc ctggctgagt gagatggcag ctggcttggc aaggggacag cacctttgtc    540
accacattat gtccctgtac cctacatgct gcgcctatac ccaggaccga tggtaactga    600
ggcggagggg aaaggagggc ctgagatggc aagtctgtcc tcctcggtgg ttcctgtgtc    660
cttcatttcc actctgcgag agtctgtgct ggaccctgga gttggtggag aaggagccag    720
tgacaagcag aggagcaaac tgtctttatc acactccatg atcccagctg ctaaaatcca    780
cactgagctc tgcttaccag ccttcttctc tcctgctgga acccagagga ggttccagca    840
gcctcagcac cacctgacac tggtaagaaa tgcagatgat caggccttac cccagaccta    900
ttgaatcaga aattctggag tggtgccctg cagcttgcat tttaaccagc cttcaggtgc    960
ttctgatgca tgctcaggtt tgagcaccac tggccacagg gaggcctagg caattcagcc   1020
ttcctctggt tgaatagctg gagaattggg aatatcagta aatacttcca atgcacctgc   1080
tacatgccag aaaaaggaaa caagaagacg cagtaggtct gagaaagtga tggggtgagc   1140
agaaacccaa agcttataga aggccatctg agtggcccct caagccggtg aattggcttt   1200
agggtttact gaaggaggtg gaaacctcag cctgcttctc gtccgggttg ttagaggagt   1260
catttagaaa gctgtaccat tctttcaata ttctcacggc tttccagtgc tcatttttcc   1320
tgctcattta tggattaaaa aaaatgcctt ggctgtatgt gtaagaaaac aacaatgcaa   1380
gtttgtagag aaagaatctg ggccttacag gtcacgttgg tttaaaattt agacatcaag   1440
cagcttagag accatgttgc caaataagct tagtaaatgc tttctaatgc ttacggaact   1500
gtggcgcttt gtgcttgcca tagtatatat aattagacaa atgagagaac acaaaggttg   1560
aacccccttcc ctctcttaat ttttgttttt tacaagcaga tttaaaattc tggctcataa   1620
tgtccttgat tcaatgttaa accattttgc ctaaatggca gcatgttcta aatgtgagcg   1680
cgctcagctt ttcaagctgc tcccgagtga cagaaattga caagctgtca ttcaagacct   1740
ttcggtggct gcctggggct ctgtttgaat tgtatctgtc tgatacttta ccatggagag   1800
tgaaaaattt gatcacatgc catgctttta attttctaaa gcaaatatgt tggaaggagc   1860
caattaatgc aaagatggac tgctggtctc atgcaactga tttaggggaa gggttcgcct   1920
aaattaataa aagatctgaa ttatagatct taacaaatac atagaatgta aaggcttaaa   1980
aggaaactga gcagcagcag gcctggggtt ggcttttaag tatctatatt taactaatag   2040
acatgaatgt tttgatttga tattagaaat gctagtgctg gagtctctga gcctactctg   2100
gctcgagagg atgccctatc taaaaaacaa aaaacaaaaa aaaaaaagaa aaaagaaaaa   2160
aagaaatgct ggtattgtaa ttctaaagtg cttcagaaat tctcaaaaat aggccaggca   2220
tggtggctca tggctgtata ccagcacttt gggaggccaa ggtgggcaaa tcacttgcag   2280
tcaggagttt gagaccagcc tggtcaacat ggtgaaaccc catctctact aaaaatacag   2340
aaattagcca ggcatggtgg cagcacctgt aatcccagct acttgggagg ctgaggcagg   2400
agaatcgcta gaacctggga ggtggaggtt gcagtgagcc aagaccgcac cactgcactc   2460
cagcctgggc aacagagtga gactctatct caaaaaaaaa aaaaaaaagt tctcaaaagt   2520
attttgaact tcctcacctt tgtcctattt tggaaggagg gggtctacat tgaagagatc   2580
atacagaaat aaattaattg ttacaaaagg aatggaatgt ctatacttct taccctattg   2640
agttacatta actgcatctt caacttaatt taaagtgctc ctcaacctaa aatatcgtca   2700
```

-continued tgtgtcttta aaaatgcata ttactaaatc tatttttttt tcagtctatc atccacactg 2760
cagcaaggtg attctgccaa aacatatctc cttaaaagcc aactggagct tctcatcagc 2820
atcaatgtga agccaaaaat ccttaggagg acagagggag tccctcacaa cctagactgg 2880
tccccttccc tccagctgcc tcaactgtcc acaggactct cttcccacct gcggccacac 2940
tgtgcaacct ggaatttccc cacctgggcg gactcatcac gtcatcacca attggatgca 3000
tcttctgctc tgtgcagctg gtgaaatctt tctcaaccct tgagatgcag cccaatcttc 3060
tcctaacatc tggattcctc tctgtcactg cattccctcc tgtcatcctg cctttgtttt 3120
cttgccctcc tttctctccc gggtgatagg cattaactaa aattaaataa aaattcagat 3180
catccttgca cttgctgcat ttcaaatgct tggcagtcac atgtagttag tggctaccct 3240
cttggacagc acagatagag attatttcca tcactgcaga aaattctaga ctttgagctt 3300
cttgaggaca ggggcttgat cattcgacac tgctttacag tgtctagcag tgtctaccct 3360
gtggcagggg ctcaggaaat ttttcctgaa ccgaacctaa ctgaactgat gtgggtttgt 3420
catcagggtg tacctgctgt taaaggaggt tacgacctct gatgctgggg tggccagagg 3480
ggatgggagt gggtctggca ctctgaggaa agggggtgaa accagctgag aagtcatctt 3540
ttacctgctg gcatggcccc agccagggtt ctgttgctat gggagaatgg gtgagtaggg 3600
atggattaca ccaccctgga tctagaggac aacctggctt gaggggcatg gggacgctg 3660 gaagtcaggg taagaagctt ggacttcatt 3690

<210> SEQ ID NO 21
<211> LENGTH: 415
<212> TYPE: DNA
<213> ORGANISM: Homo sapiens

<400> SEQUENCE: 21
ttgagatgca gcccaatctt ctcctaacat ctggattcct ctctgtcact gcattccctc 60
ctgtcatcct gcctttgttt tcttgccctc ctttctctcc cggttattaa ttaattaact 120
aaaattaaat tatttagtta atttaattaa ctaaactaat gggtgagtag ggatggatta 180
caccaccctg gatctagagg acaacctggc ttgaggggca tgggggacgc tggaagtcag 240
ggtaagaagc ttggacttca ttctactggc atggagagcc cctggaaact actgagcagt 300
agagggatag gctaagctta taggaggagc caaaattatt actgtagctc cttagatctt 360
agatcctgtg acttaggaaa ggcaatagga gcccctgagc attctgggtc ctttg 415

<210> SEQ ID NO 22
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: SNP identification no. rs10490924
<220> FEATURE:
<221> NAME/KEY: misc_feature
<222> LOCATION: (27)..(27)
<223> OTHER INFORMATION: n is g or t

<400> SEQUENCE: 22
ctttatcaca ctccatgatc ccagctncta aaatccacac tgagctctgc tt 52

<210> SEQ ID NO 23
<211> LENGTH: 52
<212> TYPE: DNA
<213> ORGANISM: Homo sapiens -continued

```
<220> FEATURE:
<221> NAME/KEY: misc_feature
<222> LOCATION: (27)..(27)
<223> OTHER INFORMATION: SNP identificatoin no. rs1048663
<220> FEATURE:
<221> NAME/KEY: misc_feature
<222> LOCATION: (27)..(27)
<223> OTHER INFORMATION: n is a or g

<400> SEQUENCE: 23

tgacttacct ctagaagact gaatagntat caggtcatcc tcctggataa tc            52


<210> SEQ ID NO 24
<211> LENGTH: 51
<212> TYPE: DNA
<213> ORGANISM: Homo sapiens
<220> FEATURE:
<221> NAME/KEY: misc_feature
<222> LOCATION: (27)..(27)
<223> OTHER INFORMATION: SNP identification no. rs11582939
<220> FEATURE:
<221> NAME/KEY: misc_feature
<222> LOCATION: (27)..(27)
<223> OTHER INFORMATION: n is c or t

<400> SEQUENCE: 24

tttaagcatc ctctgatgta tattctagac ttctcatctc tgttcttagg g             51


<210> SEQ ID NO 25
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: SNP identification no. rs1280514
<220> FEATURE:
<221> NAME/KEY: misc_feature
<222> LOCATION: (27)..(27)
<223> OTHER INFORMATION: n is a or g

<400> SEQUENCE: 25

ctcctgctca ttcctctcaa cagacanaaa caattttgtg agaattttta tg            52
```